(12) United States Patent
Feng et al.

(10) Patent No.: US 8,088,784 B2
(45) Date of Patent: Jan. 3, 2012

(54) 4-(3-AMINOPYRAZOLE) PYRIMIDINE DERIVATIVES FOR USE AS TYROSINE KINASE INHIBITORS IN THE TREATMENT OF CANCER

(75) Inventors: Xiaomei Feng, Waltham, MA (US); Huiping Guan, Waltham, MA (US); Ying Kang, Shanghai (CN); Stephanos Ioannidis, Waltham, MA (US); Bo Peng, Waltham, MA (US); Mei Su, Waltham, MA (US); Bin Wang, Longmont, CO (US); Tao Wang, Waltham, MA (US); Hai-Jun Zhang, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/713,695

(22) Filed: Feb. 26, 2010

(65) Prior Publication Data

US 2010/0160325 A1     Jun. 24, 2010

Related U.S. Application Data

(63) Continuation of application No. 12/091,382, filed as application No. PCT/GB2006/003978 on Oct. 26, 2006, now abandoned.

(60) Provisional application No. 60/731,299, filed on Oct. 28, 2005, provisional application No. 60/803,061, filed on May 24, 2006.

(51) Int. Cl.
C07D 403/14  (2006.01)
A61K 31/506  (2006.01)

(52) U.S. Cl. ......................... 514/275; 544/296
(58) Field of Classification Search .................. 544/296; 514/275
See application file for complete search history.

(56) References Cited

U.S. PATENT DOCUMENTS

| | | | |
|---|---|---|---|
| 4,038,240 A | 7/1977 | Hugl et al. | |
| 4,485,284 A | 11/1984 | Pakulis | |
| 5,147,876 A | 9/1992 | Mizuchi et al. | |
| 5,459,318 A | 10/1995 | Cacho et al. | |
| 5,521,184 A | 5/1996 | Zimmermann | |
| 6,383,553 B1 | 5/2002 | Tondar et al. | |
| 6,399,780 B1 | 6/2002 | Hudkins | |
| 6,455,525 B1 | 9/2002 | Singh et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,098,330 B2 | 8/2006 | Bebbington et al. | |
| 7,115,739 B2 | 10/2006 | Bebbington et al. | |
| 7,148,455 B2 | 12/2006 | Scalese et al. | |
| 7,183,307 B2 | 2/2007 | Hale et al. | |
| 7,279,476 B2 | 10/2007 | Tang et al. | |
| 7,390,815 B2 | 6/2008 | Davies et al. | |
| 7,427,681 B2 | 9/2008 | Bebbington et al. | |
| 7,473,691 B2 | 1/2009 | Davies et al. | |
| 7,521,453 B2 * | 4/2009 | Barlaam et al. | 514/255.05 |
| 7,528,138 B2 | 5/2009 | Knegtel et al. | |
| 7,528,142 B2 | 5/2009 | Binch et al. | |
| 7,531,536 B2 | 5/2009 | Bebbington et al. | |
| 2003/0055068 A1 | 3/2003 | Bebbington et al. | |
| 2003/0078275 A1 | 4/2003 | Bebbington et al. | |
| 2003/0079365 A1 | 5/2003 | Corak et al. | |
| 2003/0105090 A1 | 6/2003 | Bebbington et al. | |
| 2005/0038023 A1 | 2/2005 | Bebbington et al. | |
| 2005/0054638 A1 | 3/2005 | Barlaam et al. | |
| 2007/0142413 A1 | 6/2007 | Block et al. | |
| 2008/0004302 A1 | 1/2008 | Theoclitou et al. | |

(Continued)

FOREIGN PATENT DOCUMENTS

EP     1317448     5/2005

(Continued)

OTHER PUBLICATIONS

Leroith and Roberts "The Insulin-like Growth Factor System and Cancer". Cancer Letters (2003) vol. 195, 127-137.
Simone "Oncology: Introduction, Cecil Textbook of Medicine, 20th Edition" (1996), vol. 1, 1004-1010.
Ulrich et al. "Chapter 4: Crystallization". Kirk-Othmer Encyclopedia of Chemical Technology (Aug. 2002).
Vippagunta et al. "Crystalline Solids". Advanced Drug Delivery Reviews (2001), vol. 48, 3-26.

(Continued)

Primary Examiner — Deepak Rao

(57) ABSTRACT

This invention relates to novel compounds having the formula (I) and to their pharmaceutical compositions and to their methods of use. These novel compounds provide a treatment for cancer.

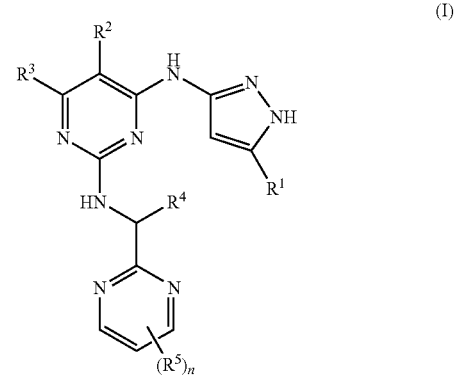

(I)

6 Claims, No Drawings

U.S. PATENT DOCUMENTS

| | | | |
|---|---|---|---|
| 2008/0108633 | A1 | 5/2008 | Claesson |
| 2008/0108669 | A1 | 5/2008 | Claesson |
| 2008/0176872 | A1 | 7/2008 | Lamb et al. |
| 2008/0194606 | A1 | 8/2008 | Scott et al. |
| 2008/0287437 | A1 | 11/2008 | Wang et al. |
| 2008/0287475 | A1 | 11/2008 | Feng et al. |
| 2009/0005396 | A1 | 1/2009 | Claesson |
| 2010/0152219 | A1 | 6/2010 | Block et al. |

FOREIGN PATENT DOCUMENTS

| | | |
|---|---|---|
| EP | 1317444 | 5/2006 |
| EP | 1317447 | 5/2006 |
| EP | 1317449 | 5/2006 |
| EP | 1317452 | 5/2006 |
| EP | 1318997 | 5/2006 |
| EP | 1345922 | 5/2006 |
| EP | 1345926 | 5/2006 |
| EP | 1345927 | 5/2006 |
| EP | 1345929 | 5/2006 |
| EP | 1353916 | 9/2006 |
| EP | 1345928 | 2/2007 |
| EP | 1876178 | 1/2008 |
| EP | 1686999 | 7/2009 |
| WO | WO 95/09852 | 4/1995 |
| WO | WO 97/09325 | 3/1997 |
| WO | WO 97/19065 | 5/1997 |
| WO | WO 98/38171 | 9/1998 |
| WO | WO 99/41253 | 8/1999 |
| WO | WO 00/12485 | 3/2000 |
| WO | WO 00/14552 | 3/2000 |
| WO | WO 00/16067 | 3/2000 |
| WO | WO 00/27825 | 5/2000 |
| WO | WO 00/35455 | 6/2000 |
| WO | WO 00/39101 | 7/2000 |
| WO | WO 00/53595 | 9/2000 |
| WO | WO 00/63182 | 10/2000 |
| WO | WO 00/73344 | 12/2000 |
| WO | WO 00/78731 | 12/2000 |
| WO | WO 01/17995 | 3/2001 |
| WO | WO 01/22938 | 4/2001 |
| WO | WO 01/47921 | 7/2001 |
| WO | WO 01/60816 | 8/2001 |
| WO | WO 01/64655 | 9/2001 |
| WO | WO 01/64656 | 9/2001 |
| WO | WO 01/85699 | 11/2001 |
| WO | WO 02/18346 | 3/2002 |
| WO | WO 02/20479 | 3/2002 |
| WO | WO 02/20513 | 3/2002 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/50071 | 6/2002 |
| WO | WO 02/059111 | 8/2002 |
| WO | WO 02/064096 | 8/2002 |
| WO | WO 03/026665 | 4/2003 |
| WO | WO 03/027111 | 4/2003 |
| WO | WO 03/048133 | 6/2003 |
| WO | WO 2004/037814 | 5/2004 |
| WO | WO 2005/016893 | 2/2005 |
| WO | WO 2005/048133 | 5/2005 |
| WO | WO 2005/049033 | * 6/2005 |
| WO | WO 2005/095400 | 10/2005 |
| WO | WO 2005/103010 | 11/2005 |
| WO | WO 2006/037117 | 4/2006 |
| WO | WO 2006/048080 | 5/2006 |
| WO | WO 2006/067614 | 6/2006 |
| WO | WO 2006/074057 | 7/2006 |
| WO | WO 2006/082392 | 8/2006 |
| WO | WO 2006/087530 | 8/2006 |
| WO | WO 2006/087538 | 8/2006 |
| WO | WO 2006/115452 | 11/2006 |
| WO | WO 2006/123113 | 11/2006 |
| WO | WO 2007/049041 | 5/2007 |
| WO | WO 2007/071348 | 6/2007 |
| WO | WO 2008/135785 | 11/2008 |

OTHER PUBLICATIONS

West "Chapter 10: Solid Solutions". Solid State Chemistry and Its Applications (1988), 358 & 365.

Aimone et al. "Antinociceptive Activity of Selective Tyrosine Kinase Inhibitors in the Rat". Abstracts of the Annual Meeting of the Society for Neuroscience (2000), vol. 26, No. 1-2, 1692, XP008129558.

Alferez et al "Inhibiting Signaling by erbB Receptor Tyrosine Kinases with AZD8931, a Potent Reversible small Molecule Inhibitor, Reduces Intestinal Adenoma Formation in the ApcMin/+Mouse Model". EORTC-NCI-AACR (2010), Abstract 471.

Alferez et al "Inhibiting Signaling by erbB Receptor Tyrosine Kinases with AZD8931, a Potent Reversible small Molecule Inhibitor, Reduces Intestinal Adenoma Formation in the ApcMin/+Mouse Model". EORTC-NCI-AACR (2010), Poster.

Blowers "AZD8931". Iaslc Annual Targeted Therapies of the Treatment of Lung Cancer Meeting (2011), Santa Monica, CA, PowerPoint Presentation.

Breault et al. "Cyclin-Dependent Kinase 4 Inhibitors as a Treatment for Cancer. Part 2: Identification and Optimisation of Substituted 2, 4-Bis Anilino Pyrimidines". Bioorganic & Medicinal Chemistry Letters (2003), vol. 13, 2961-2966.

Cristofanilli et al. "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

El Kerdaway et al. "2, 4-Bis (substituted)-5-nitropyrimidines of Expected Diuretic Action". Egypt J. Chem (1986), vol. 92, No. 2, 247-251.

Hefti et al. "Novel Class of Pain Drugs Based on Antagonism of NGF". Trends in Pharmacological Sciences (2006), vol. 27, No. 2, 85-91.

Hickinson et al. "AZD8931, an Equipotent, Reversible Inhibitor of Signaling by Epidermal Growht Factor Receptor, ERBB2 (HER2), and ERBB3: A Unique Agent for Simultaneous ERBB Receptor Blockage in Cancer", Clinical Cancer Research 16:1159-1169 (2010).

International Search Report for corresponding PCT application No. PCT/GB2006/000334 May, 2006.

Keilholz et al. "Phase I Dose-Finding Study of Monotherapy with AZD8931, an Inhibitor of erbB1, 2 and 3 Signaling, in Patients with Advanced Solid Tumors". J Clin Oncol. (2011), vol. 29, Abstract 3097.

Keilholz et al. "Phase I Dose-Finding Study of Monotherapy with AZD8931, an Inhibitor of erbB1, 2 and 3 Signaling, in Patients with Advanced Solid Tumors". ASCO (2011), Poster.

Klinowska et al. "AZD8931, an Equipotent, Reversible Inhibitor of erbB1, erbB2 and erbB3 Receptor Signaling: Characterisation of Pharmacological Profile". European Journal of Cancer Supplements (2009), vol. 7, No. 2, 127.

Lopez-Martin et al. "Phase I Dose-Finding Study of AZD8931, an Inhibitor of erbB1, 2 and 3 Receptor Signaling, in Combination with Paclitaxel". J Clin. Oncol. (2011), vol. 29, Abstract 3105.

Lopez-Martin et al. "Phase I Dose-Finding Study of AZD8931, an Inhibitor of erbB1, 2 and 3 Receptor Signaling, in Combination with Paclitaxel". ASCO (2011), Poster.

Marshall et al. "Evaluation of AZD8931, an Equipotent Inhibitor of erbB1, erbB2 and erbB3 Receptor Signaling, on Ligand Stimulated Breast Cancer Cell Lines with Differing Levels of erbB2 Expression". SABCS (2009), Abstract 5059.

Normanno et al. "Target-based therapies in breast cancer: current status and future perspectives". Endocr Relat Cancer (2009), vol. 16(3): 675-702.

Parrizas et al. "Specific Inhibition of Insulin-Like Growth Factor-1 and Insulin Receptor Tyrosine Kinase Activity and Biological Function by Tyrphostins". Endocrinology (1997), vol. 138, No. 4, 1427-1433.

Pierce et al. "CH . . . O and CH . . . N Hydrogen Bonds in Ligand Design: A Novel Quinazolin-4-ylthiazol-2-ylamine Protein Kinase Inhibitor". J. Med. Chem. (2005), vol. 48, 1278-1281.

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Thress et al. "Identification and Preclinical Characterization of AZ-23, a Novel, Selective, and Orally Bioavailable Inhibitor of the Trk Kinase Pathway". Molecular Cancer Therapeutics (2009) vol. 8, No. 7, 1818-1827.

Wang et al. "Identification of 4-Aminopyrazolylpyrimidines as Potent Inhibitors of Trk Kinases". J. Med. Chem. (2008), vol. 51, No. 15, 4672-4684, ACS Publications, DC, US.

Wang et al. "Trik Kinase Inhibitors as New Treatments for Cancer and Pain". Expert Opin. Ther. Patents (2009), vol. 19, No. 3, 305-319.

Winston et al. "Suppression of Neuronal Tyrosine Kinase Activity in Associated with Improvement in Pain Responses and Inhibition of Nociceptive Gene Expression in Pancreatitis". Abstracts of the Annual Meeting of the Society for Neuroscience (2001), vol. 27, 2162, XP008129567.

* cited by examiner

4-(3-AMINOPYRAZOLE) PYRIMIDINE DERIVATIVES FOR USE AS TYROSINE KINASE INHIBITORS IN THE TREATMENT OF CANCER

CROSS-REFERENCE TO RELATED APPLICATIONS

This application is a continuation of U.S. application Ser. No. 12/091,382, filed Apr. 24, 2008, now abandoned which is a U.S. National Stage under 35 U.S.C. §371 of International Application No. PCT/GB2006/003978, filed Oct. 26, 2006, which claims priority under 35 U.S.C. §119(e) to U.S. Provisional Application No. 60/731,299, filed Oct. 28, 2005, and to U.S. Provisional Application No. 60/803,061, filed on May 24, 2006.

FIELD OF THE INVENTION

The present invention relates to novel pyrazole derivatives, their pharmaceutical compositions and methods of use. In addition, the present invention relates to therapeutic methods for the treatment and prevention of cancers and to the use of these pyrazole derivatives in the manufacture of medicaments for use in the treatment and prevention of cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified. Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al *Current Opinion in Neurobiology*, 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumours express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeraratna, A. T. et al *The Prostate*, 2000, 45, I40-I48).

Furthermore, very recent literature also shows that over-expression, activation, amplification and/or mutation of Trk's are associated with secretory breast carcinoma (*Cancer Cell*, 2002, 2, 367-376), colorectal cancer (Bardelli et al *Science*, 2003, 300, 949-949) and ovarian cancer (Davidson, B. et al *Clinical Cancer Research*, 2003, 9, 2248-2259).

There are a few reports of selective Trk tyrosine kinase inhibitors. Cephalon described CEP-751, CEP-701 (George, D. et al *Cancer Research*, 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A). Pfizer also recently published certain isothiazole Trk A inhibitors (Bioorg. Med. Chem. Lett. 2006, 16, 3444-3448).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO0348133). AstraZeneca have also reported Trk inhibitors in International Applications WO 2005/049033, WO 2005/103010, WO 2006/082392, WO 2006/087530, and WO 2006/087538.

Another such group is the JAK family. The JAK (Janus-associated kinase)/STAT (signal transducers and activators or transcription) signalling pathway is involved in a variety of hyperproliferative and cancer related processes including cell-cycle progression, apoptosis, angiogenesis, invasion, metastasis and evasion of the immune system (Haura et al., Nature Clinical Practice Oncology, 2005, 2(6), 315-324; Verna et al., Cancer and Metastasis Reviews, 2003, 22, 423-434).

The JAK family consists of four non-receptor tyrosine kinases Tyk2, JAK1, JAK2, and JAK3, which play a critical role in cytokine- and growth factor mediated signal transduction. Cytokine and/or growth factor binding to cell-surface receptor(s), promotes receptor dimerization and facilitates activation of receptor-associated JAK by autophosphorylation. Activated JAK phosphorylates the receptor, creating docking sites for SH2 domain-containing signalling proteins, in particular the STAT family of proteins (STAT1, 2, 3, 4, 5a, 5b and 6). Receptor-bound STATs are themselves phosphorylated by JAKs, promoting their dissociation from the receptor, and subsequent dimerization and translocation to the nucleus. Once in the nucleus, the STATs bind DNA and cooperate with other transcription factors to regulate expression of a number of genes including, but not limited to, genes encoding apoptosis inhibitors (e.g. Bcl-XL, Mcl-1) and cell cycle regulators (e.g. Cyclin D1/D2, c-myc) (Haura et al., Nature Clinical Practice Oncology, 2005, 2(6), 315-324; Verna et al., Cancer and Metastasis Reviews, 2003, 22, 423-434).

Over the past decade, a considerable amount of scientific literature linking constitutive JAK and/or STAT signalling with hyperproliferative disorders and cancer has been published. Constitutive activation of the STAT family, in particular STAT3 and STAT5, has been detected in a wide range of cancers and hyperproliferative disorders (Haura et al., Nature Clinical Practice Oncology, 2005, 2(6), 315-324). Furthermore, aberrant activation of the JAK/STAT pathway provides an important proliferative and/or anti-apoptotic drive downstream of many kinases (e.g. Flt3, EGFR) whose constitutive activation have been implicated as key drivers in a variety of cancers and hyperproliferative disorders (Tibes et al., Annu Rev Pharmacol Toxicol 2550, 45, 357-384; Choudhary et al., International Journal of Hematology 2005, 82(2), 93-99; Sordella et al., Science 2004, 305, 1163-1167). In addition, impairment of negative regulatory proteins, such as the suppressors of cytokine signalling (SOCS) proteins, can also influence the activation status of the JAK/STAT signalling pathway in disease (J C Tan and Rabkin R, Pediatric Nephrology 2005, 20, 567-575).

Several mutated forms of JAK2 have been identified in a variety of disease settings. For example, translocations resulting in the fusion of the JAK2 kinase domain with an oligomerization domain, TEL-JAK2, Bcr-JAK2 and PCM1-JAK2, have been implicated in the pathogenesis of various heamatologic malignancies (S D Turner and Alesander D R, Leukemia, 2006, 20, 572-582). More recently, a unique acquired mutation encoding a valine-to-phenylalanine (V617F) substitution in JAK2 was detected in a significant number of polycythemia vera, essential thrombocythemia and idiopathic myelofibrosis patients and to a lesser extent in several other diseases. The mutant JAK2 protein is able to activate downstream signalling in the absence of cytokine stimulation, resulting in autonomous growth and/or hypersensitivity to cytokines and is believed to play a critical role in driving these diseases (M J Percy and McMullin M F, Hematological Oncology 2005, 23(3-4), 91-93).

JAKs (in particular JAK3) play an important biological roles in the immunosuppressive field and there are reports of using JAK kinase inhibitors as tools to prevent organ transplant rejections (Changelian, P. S. et al, Science, 2003, 302, 875-878). Merck (Thompson, J. E. et al Bioorg. Med. Chem. Lett. 2002, 12, 1219-1223) and Incyte (WO2005/105814) reported imidazole based JAK2/3 inhibitors with enzyme potency at single nM levels. Recent Vertex described azaindoles as JAK inhibitors (WO2005/95400). AstraZeneca have published quinoline-3-carboxamides as JAK3 inhibitors (WO2002/92571).

In addition to the above, Vertex Pharmaceuticals have described pyrazole compounds as inhibitors of GSK3, Aurora, etc. in WO2002/50065, WO2002/62789, WO2003/027111 and WO2004/37814; and AstraZeneca have reported pyrazole compounds as inhibitors against IGF-1 receptor kinase—WO2003/48133—and Trk in WO2005/049033 and WO2005/103010.

SUMMARY OF THE INVENTION

In accordance with the present invention, the applicants have hereby discovered novel pyrazole compounds, or pharmaceutically acceptable salts thereof, which possess Trk kinase inhibitory activity and are accordingly useful for their anti-proliferation and/or proapoptotic (such as anti-cancer) activity and in methods of treatment of the human or animal body. The invention also relates to processes for the manufacture of said pyrazole compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such pyrazole compounds, or pharmaceutically acceptable salts thereof, in the treatment of cancer.

The properties of the compounds claimed in this invention are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds, or pharmaceutically acceptable salts thereof, of the invention are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposi sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

In accordance with the present invention, the applicants have further hereby discovered novel compounds, and pharmaceutically acceptable salts thereof, which possess JAK kinase inhibitory activity and are accordingly useful for their anti-proliferation and/or pro-apoptotic activity and in methods of treatment of the human or animal body. The invention also relates to processes for the manufacture of said compound, or pharmaceutically acceptable salts thereof, to pharmaceutical compositions containing it and to its use in the manufacture of medicaments for use in the production of an anti-proliferation and/or pro-apoptotic effect in warm-blooded animals such as man. Also in accordance with the present invention the applicants provide methods of using said compound, or pharmaceutically acceptable salts thereof, in the treatment of myeloproliferative disorders, myelodysplastic syndrome and cancer.

The properties of the compounds claimed in this invention are expected to be of value in the treatment of myeloproliferative disorders, myelodysplastic syndrome, and cancer by inhibiting the tyrosine kinases, particularly the JAK family and more particularly JAK2. Methods of treatment target tyrosine kinase activity, particularly the JAK family activity and more particularly JAK2 activity, which is involved in a variety of myeloproliferative disorders, myelodysplastic syndrome and cancer related processes. Thus, inhibitors of tyrosine kinase, particularly the JAK family and more particularly JAK2, are expected to be active against myeloproliferative disorders such as chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and neoplastic disease such as carcinoma of the breast, ovary, lung, colon, prostate or other tissues, as well as leukemias, myelomas and lymphomas, tumours of the central and peripheral nervous system, and other tumour types such as melanoma, fibrosarcoma and osteosarcoma. Tyrosine kinase inhibitors, particularly the JAK family inhibitors and more particularly JAK2 inhibitors are also expected to be useful for the treatment other proliferative diseases including but not limited to autoimmune, inflammatory, neurological, and cardiovascular diseases.

Furthermore, the compound, or pharmaceutically acceptable salts thereof, of the invention is expected to be of value in the treatment or prophylaxis of against myeloproliferative disorders selected from chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia; particularly myeloma, leukemia, ovarian cancer, breast cancer and prostate cancer.

DETAILED DESCRIPTION OF THE INVENTION

Accordingly, the present invention provides a compound of formula (I):

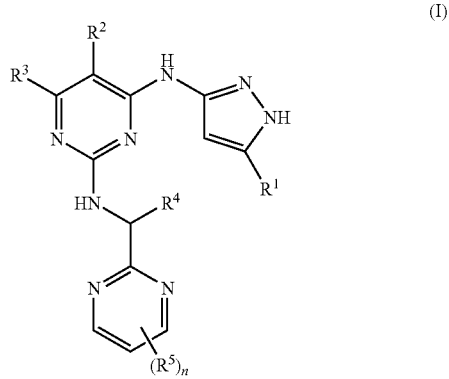

(I)

wherein:

$R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, ($C_{1-6}$alkyl)$_2$N—S(O)$_2$—NH—, ($C_{1-6}$alkyl)NH—S(O)$_2$—NH—, NH$_2$—S(O)$_2$—NH—, ($C_{1-6}$alkyl)$_2$N—S(O)$_2$—N($C_{1-6}$alkyl)-, ($C_{1-6}$alkyl)NH—S(O)$_2$—N($C_{1-6}$alkyl)-, NH$_2$—S(O)$_2$—N($C_{1-6}$alkyl)-, N—($C_{1-6}$alkyl)-N—($C_{1-6}$alkylsulphonyl)amino, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

In another aspect, the invention relates to compounds of formula (I), wherein: $R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkoxycarbonyl, carbocyclyl or heterocyclyl; wherein $R^4$ may be optionally substituted on carbon by one or more $R^{11}$); and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

In another aspect, the invention relates to compounds of formula (I), wherein: $R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)

sulphamoyl, N,N—($C_{1-6}$alkyl)$_2$sulphamoyl, N—($C_{1-6}$alkyl)-N—($C_{1-6}$alkylsulphonyl)amino, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

Particular values of the variable groups contained in formula (I) are as follows. Such values may be used, where appropriate, with any of the definitions, claims or embodiments defined hereinbefore or hereinafter.

$R^1$ is selected from $C_{1-6}$alkyl, $C_{1-6}$alkoxy, 3-5-membered carbocyclyl, and N,N—($C_{1-6}$alkyl)$_2$-amino, wherein $R^1$ may be optionally substituted on carbon by one or more $R^6$; and wherein $R^6$ is halo.

$R^1$ is $C_{1-6}$alkoxy or 3-5-membered carbocyclyl.

$R^1$ is selected from $C_{1-6}$alkyl, $C_{1-6}$alkoxy or 3-5-membered carbocyclyl.

$R^1$ is $C_{1-6}$alkyl or $C_{1-6}$alkoxy.

$R^1$ is 3-5 membered carbocyclyl.

$R^1$ is N,N($C_{1-6}$alkyl)$_2$amino.

$R^1$ is $C_{1-6}$alkyl.

$R^1$ is $C_{1-4}$alkyl.

$R^1$ is $C_{1-6}$alkoxy.

$R^1$ is selected from methyl, methoxy, trifluoroethoxy, isopropoxy, cyclopropyl, and N,N-dimethylamino;

$R^1$ is isopropoxy or cyclopropyl.

$R^1$ is methyl, methoxy, isopropoxy or cyclopropyl.

$R^1$ is selected from methyl, methoxy, isopropoxy, N,N-dimethylamino, and cyclopropyl.

$R^1$ is isopropoxy.

$R^1$ is methyl.

$R^1$ is ethyl.

$R^1$ is selected from methyl, ethyl, propyl, and butyl.

$R^1$ is selected from $C_{1-4}$alkyl, $C_{1-4}$alkoxy, and cyclopropyl.

$R^1$ is methoxy.

$R^1$ is cyclopropyl. $R^1$ is N,N-dimethylamino.

$R^2$ is selected from hydrogen, halo, nitro, and $C_{1-6}$alkyl, wherein $R^2$ may be optionally substituted on carbon by one or more $R^8$; and wherein $R^8$ is halo.

$R^2$ is selected from hydrogen, chloro, fluoro, bromo, nitro, and trifluoromethyl.

$R^2$ is halo.

$R^2$ is $C_{1-6}$alkyl, wherein $R^2$ may be optionally substituted on carbon by one or more $R^8$; and wherein $R^8$ is halo.

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$;

and wherein if said heterocyclyl contains an —NH— moiety that nitrogen may be optionally substituted by a group selected from $R^9$.

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, N—($C_{1-6}$alkyl)-N—($C_{1-6}$alkylsulphonyl)amino, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$.

$R^2$ and $R^3$ are independently selected from hydrogen, halo, N—($C_{1-6}$alkyl)-N—($C_{1-6}$alkylsulphonyl)amino, or heterocyclyl-$R^{21}$—; wherein $R^{21}$ is a direct bond.

$R^2$ and $R^3$ are independently selected from hydrogen and halo.

$R^2$ and $R^3$ are independently selected from hydrogen and chloro.

$R^2$ and $R^3$ are independently selected from hydrogen, fluoro, chloro, bromo, N-methyl-N-mesylamino and morpholino.

$R^2$ is halo and $R^3$ is hydrogen.

$R^2$ is chloro and $R^3$ is hydrogen.

$R^2$ is chloro or fluoro and $R^3$ is hydrogen. $R^3$ is selected from hydrogen, halo, cyano, N—($C_{1-6}$alkyl)-N—($C_{1-6}$alkylsulphonyl)amino, $C_{1-6}$alkyl, ($C_{1-6}$alkyl)$_2$N—S(O)$_2$—N($C_{1-6}$alkyl)-, and heterocyclyl-$R^{21}$—, wherein $R^3$ may be optionally substituted on carbon by one or more $R^8$; wherein $R^8$ is halo; and wherein $R^{21}$ is a bond.

$R^3$ is hydrogen.

$R^3$ is halo.

$R^3$ is selected from N—($C_{1-6}$alkyl)-N—($C_{1-6}$alkylsulphonyl)amino and ($C_{1-6}$alkyl)$_2$N—S(O)$_2$—N($C_{1-6}$alkyl)-.

$R^3$ is selected from heterocyclyl-$R^{21}$—, wherein $R^3$ may be optionally substituted on carbon by one or more $R^8$ wherein $R^8$ is halo; and wherein $R^{21}$ is a bond.

$R^3$ is selected from hydrogen, chloro, cyano, trifluoromethyl, (CH$_3$)$_2$N—S(O)$_2$—N(CH$_3$)—, N-methyl-N-mesylamino, and morpholino.

$R^3$ is (CH$_3$)$_2$N—S(O)$_2$—N(CH$_3$)—.

$R^3$ is N-methyl-N-mesylamino, $R^3$ is morpholino.

$R^4$ is $C_{1-6}$alkyl.

$R^4$ is methyl.

$R^5$ is halo.

$R^5$ is fluoro.

n=1.

$R^{19}$ and $R^{21}$ are independently selected from —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2.

Therefore in a further aspect of the invention there is provided a compound of formula (I) (as depicted herein above) wherein:

$R^1$ is selected from $C_{1-6}$alkyl, $C_{1-6}$alkoxy or 3-5-membered carbocyclyl;

$R^2$ and $R^3$ are independently selected from hydrogen, halo, N—($C_{1-6}$alkyl)-N—($C_{1-6}$alkylsulphonyl)amino, or heterocyclyl-$R^{21}$—;

$R^4$ is $C_{1-6}$alkyl;

$R^5$ is halo;

n=1;

$R^{21}$ is a direct bond;

or a pharmaceutically acceptable salt thereof.

Therefore in a further aspect of the invention there is provided a compound of formula (I) (as depicted herein above) wherein:

$R^1$ is $C_{1-6}$alkoxy;

$R^2$ and $R^3$ are independently selected from hydrogen and halo;

$R^4$ is $C_{1-6}$alkyl;

$R^5$ is halo;

n=1;

or a pharmaceutically acceptable salt thereof.

Therefore in a further aspect of the invention there is provided a compound of formula (I) (as depicted herein above) wherein:

$R^1$ is methyl, methoxy, isopropoxy or cyclopropyl;

$R^2$ and $R^3$ are independently selected from hydrogen, fluoro, chloro, bromo, N-methyl-N-mesylamino and morpholino;

$R^4$ is methyl;

$R^5$ is fluoro; and n=1;

or a pharmaceutically acceptable salt thereof.

Therefore in a further aspect of the invention there is provided a compound of formula (I) (as depicted herein above) wherein:

$R^1$ is selected from $C_{1-6}$alkyl, $C_{1-6}$alkoxy, 3-5-membered carbocyclyl, and N,N—($C_{1-6}$alkyl)$_2$-amino, wherein $R^1$ may be optionally substituted on carbon by one or more $R^6$;

$R^2$ is selected from hydrogen, halo, nitro, and $C_{1-6}$alkyl, wherein $R^2$ may be optionally substituted on carbon by one or more $R^8$;

$R^3$ is selected from hydrogen, halo, cyano, N—($C_{1-6}$alkyl)-N—($C_{1-6}$alkylsulphonyl)amino, $C_{1-6}$alkyl, ($C_{1-6}$alkyl)$_2$N—S(O)$_2$—N($C_{1-6}$alkyl)-, and heterocyclyl-$R^{21}$—, wherein $R^3$ may be optionally substituted on carbon by one or more $R^8$;

$R^4$ is $C_{1-6}$alkyl;

$R^5$ is halo;

$R^6$ is halo;

$R^8$ is halo;

$R^{21}$ is a bond; and n=1;

or a pharmaceutically acceptable salt thereof.

Therefore in a further aspect of the invention there is provided a compound of formula (I) (as depicted herein above) wherein:

$R^1$ is selected from methyl, methoxy, trifluoroethoxy, isopropoxy, cyclopropyl, and N,N-dimethylamino;

$R^2$ is selected from hydrogen, chloro, fluoro, bromo, nitro, and trifluoromethyl;

$R^3$ is selected from hydrogen, chloro, cyano, trifluoromethyl, (CH$_3$)$_2$N—S(O)$_2$—N(CH$_3$)—, N-methyl-N-mesylamino, and morpholino;

$R^4$ is methyl;

$R^5$ is fluoro; and n is 1;

or a pharmaceutically acceptable salt thereof.

Therefore in a further aspect of the invention there is provided a compound of formula (I) (as depicted herein above) wherein:

$R^1$ is selected from $C_{1-6}$alkoxy, wherein $R^1$ may be optionally substituted on carbon by one or more $R^6$;

$R^2$ is selected from hydrogen and halo;

$R^3$ is selected from hydrogen, halo, and heterocyclyl-$R^{21}$—;

R⁴ is $C_{1-6}$alkyl;
R⁵ is halo;
R⁶ is halo;
R²¹ is a bond;
n is 1;
or a pharmaceutically acceptable salt thereof.

Therefore in a further aspect of the invention there is provided a compound of formula (I) (as depicted herein above) wherein:

R¹ is selected from $C_{1-4}$alkyl, $C_{1-4}$alkoxy, and cyclopropyl;
R² is selected from hydrogen, halo, nitro, and $C_{1-6}$alkyl, wherein R² may be optionally substituted on carbon by one or more R⁸;
R³ is selected from hydrogen, halo, cyano, N—($C_{1-6}$alkyl)-N—($C_{1-6}$alkylsulphonyl)amino, $C_{1-6}$alkyl, ($C_{1-6}$alkyl)₂N—S(O)₂—N($C_{1-6}$alkyl)-, and heterocyclyl-R²¹—, wherein R³ may be optionally substituted on carbon by one or more R⁸;
R⁴ is $C_{1-6}$alkyl;
R⁵ is halo;
R⁶ is halo;
R⁸ is halo;
R²¹ is a bond; and
n=1;
or a pharmaceutically acceptable salt thereof.

In another aspect of the invention, preferred compounds of the invention are any one of the Examples or a pharmaceutically acceptable salt thereof.

In another aspect of the invention, preferred compounds of the invention are any one of:
N-{5-fluoro-2-{[(1S)-1-(5-fluoropyrimidin-2-yl)ethyl]amino}-6-[(5-methyl-1H-pyrazol-3-yl)amino]pyrimidin-4-yl}-N-methylmethanesulfonamide;
5-Fluoro-N2-[(1S)-1-(5-fluoropyrimidin-2-yl)ethyl]-N4-(5-methyl-1H-pyrazol-3-yl)pyrimidine-2,4-diamine;
5-Chloro-N2-[(1S)-1-(5-fluoropyrimidin-2-yl)ethyl]-N4-(5-methoxy-1H-pyrazol-3-yl)pyrimidine-2,4-diamine;
N2-[(1S)-1-(5-fluoropyrimidin-2-yl)ethyl]-N4-(5-methoxy-1H-pyrazol-3-yl)-6-(trifluoromethyl)pyrimidine-2,4-diamine;
N2-[(1S)-1-(5-Fluoropyrimidin-2-yl)ethyl]-N4-(5-methyl-1H-pyrazol-3-yl)-6-morpholin-4-ylpyrimidine-2,4-diamine;
5-Chloro-N4-(5-cyclopropyl-1H-pyrazol-3-yl)-N2-[(1S)-1-(5-fluoropyrimidin-2-yl)ethyl]pyrimidine-2,4-diamine;
5-Fluoro-N2-[(1S)-1-(5-fluoropyrimidin-2-yl)ethyl]-N4-(5-methyl-1H-pyrazol-3-yl)pyrimidine-2,4-diamine;
5-bromo-N2-[(1S)-1-(5-fluoropyrimidin-2-yl)ethyl]-N4-(5-methoxy-1H-pyrazol-3-yl)pyrimidine-2,4-diamine;
N4-(5-Cyclopropyl-1H-pyrazol-3-yl)-5-fluoro-N2-[(1S)-1-(5-fluoropyrimidin-2-yl)ethyl]pyrimidine-2,4-diamine;
N2-[(1S)-1-(5-fluoropyrimidin-2-yl)ethyl]-5-methyl-N4-(5-methyl-1H-pyrazol-3-yl)pyrimidine-2,4-diamine;
N-{5-chloro-2-{[(1S)-1-(5-fluoropyrimidin-2-yl)ethyl]amino}-6-[(5-methoxy-1H-pyrazol-3-yl)amino]pyrimidin-4-yl}-N-methylmethanesulfonamide;
N-{5-chloro-2-{[(1S)-1-(5-fluoropyrimidin-2-yl)ethyl]amino}-6-[(5-methyl-1H-pyrazol-3-yl)amino]pyrimidin-4-yl}-N-methylmethanesulfonamide;
N2-[(1S)-1-(5-fluoropyrimidin-2-yl)ethyl]-N4-(5-methoxy-1H-pyrazol-3-yl)-6-morpholin-4-ylpyrimidine-2,4-diamine;
5-chloro-N2-[(1S)-1-(5-fluoropyrimidin-2-yl)ethyl]-N4-(5-methoxy-1H-pyrazol-3-yl)-6-morpholin-4-ylpyrimidine-2,4-diamine;
5-fluoro-N2-[(1S)-1-(5-fluoropyrimidin-2-yl)ethyl]-N4-(5-methyl-1H-pyrazol-3-yl)-6-morpholin-4-ylpyrimidine-2,4-diamine; and
5-fluoro-N2-[(1S)-1-(5-fluoropyrimidin-2-yl)ethyl]-N4-(5-methoxy-1H-pyrazol-3-yl)-6-morpholin-4-ylpyrimidine-2,4-diamine;
or a pharmaceutically acceptable salt thereof.

In an additional embodiment the present invention provides a compound of formula (I), or a pharmaceutically acceptable salt thereof, for use as a medicament.

In an additional embodiment the present invention provides a compound of formula (I), or a pharmaceutically acceptable salt thereof, for use in the manufacture of a medicament for use in the inhibition of Trk activity.

In an additional embodiment the present invention provides a compound of formula (I), or a pharmaceutically acceptable salt thereof, for use in the manufacture of a medicament for use in the treatment or prophylaxis of cancer.

In an additional embodiment the present invention provides a compound of the formula (I), or a pharmaceutically acceptable salt thereof, for use in the manufacture of a medicament for use in the treatment of cancer in a warm-blooded animal such as man.

In an additional embodiment the present invention provides a compound of the formula (I), or a pharmaceutically acceptable salt thereof, for use in the manufacture of a medicament for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the manufacture of a medicament for use in the production of an anti-proliferative effect.

In an additional embodiment, the present invention provides the use of a compound of formula (I), or a pharmaceutically acceptable salt thereof, in the manufacture of a medicament for use in the production of an anti-proliferative effect in a warm-blooded animal such as man.

In an additional embodiment the present invention provides the use of a compound of formula (I), or a pharmaceutically acceptable salt thereof, in the manufacture of a medicament for use in the production of an pro-apoptotic effect in a warm-blooded animal such as man.

In an additional embodiment the present invention provides the use of a compound of formula (I), or a pharmaceutically acceptable salt thereof, in the manufacture of a medicament for use in the treatment of myeloproliferative disorders, myelodysplastic syndrome, and cancer in a warm-blooded animal such as man.

In an additional embodiment the present invention provides the use of a compound of formula (I), or a pharmaceutically acceptable salt thereof, in the manufacture of a medicament for use in the treatment of chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia.

In an additional embodiment, the present invention provides the use of a compound of formula (I), or a pharmaceutically acceptable salt thereof, in the manufacture of a medicament for use in the treatment of cancer, wherein said cancer is selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia.

In an additional embodiment the present invention provides a method of inhibiting Trk activity comprising administering to a host in need of such treatment a therapeutically effective amount of a compound of formula (I), or a pharmaceutically acceptable salt thereof.

In an additional embodiment the present invention provides a method for the treatment of cancer comprising administering to a host in need of such treatment a therapeutically effective amount of a compound of formula (I), or a pharmaceutically acceptable salt thereof.

In an additional embodiment the present invention provides a method for the treatment or prophylaxis of cancer comprising administering a therapeutically effective amount of a compound of formula (I) or a pharmaceutically acceptable salt thereof.

In an additional embodiment the present invention provides a method for the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment the present invention provides a method of producing an anti-proliferative effect in a warm-blooded animal, such as man, in need of such treatment which comprises administering to said animal an effective amount of a compound of formula (I), or a pharmaceutically acceptable salt thereof.

In an additional embodiment, the present invention provides a method for producing a pro-apoptotic effect in a warm-blooded animal, such as man, in need of such treatment, said method comprising administering to said animal an effective amount of a compound of formula (I), or a pharmaceutically salt thereof.

In an additional embodiment, the present invention provides a method of treating myeloproliferative disorders, myelodysplastic syndrome, and cancer in a warm-blooded animal, such as man, in need of such treatment, said method comprising administering to said animal an effective amount of a compound of formula (I), or a pharmaceutically acceptable salt thereof.

In an additional embodiment, the present invention provides a method of treating chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma, and leukaemia in a warm-blooded animal, such as man, in need of such treatment, said method comprising administering to said animal an effective amount of a compound of formula (I).

In an additional embodiment, the present invention provides a method of treating myeloma, leukemia, ovarian cancer, breast cancer, and prostate cancer in a warm-blooded animal, such as man, in need of such treatment, said method comprising administering to said animal an effective amount of a compound of formula (I).

In an additional embodiment, the present invention provides a method of treating myeloproliferative disorders, myelodysplastic syndrome and cancers (solid and heamatologic tumors), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acromegaly, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment, the present invention provides a method of treating cancer in a warm-blooded animal, such as man, in need of such treatment, said method comprising administering to said animal an effective amount of a compound of formula (I), or a pharmaceutically acceptable salt thereof, wherein said cancer is selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia.

In an additional embodiment, the present invention provides a method of producing of a JAK inhibitory effect in a warm-blooded animal, such as man, in need of such treatment, said method comprising administering to said animal an effective amount of a compound of formula (I), or a pharmaceutically acceptable salt thereof.

In an additional embodiment the present invention provides a pharmaceutical composition comprising a compound of formula (I), or a pharmaceutically acceptable salt thereof, together with at least one pharmaceutically acceptable carrier, diluent or excipient.

In an additional embodiment the present invention provides a pharmaceutical composition comprising a compound of formula (I), or a pharmaceutically acceptable salt thereof, together with at least one pharmaceutically acceptable carrier, diluent or excipient for use in the inhibition of Trk activity.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In an additional embodiment the present invention provides a pharmaceutical composition comprising a compound of formula (I), or a pharmaceutically acceptable salt thereof, together with at least one pharmaceutically acceptable carrier, diluent or excipient for use in the production of an anti-proliferative effect in a warm-blooded animal such as man.

In an additional embodiment, the present invention provides a pharmaceutical composition comprising a compound of formula (I), or a pharmaceutically acceptable salt thereof, and at least one pharmaceutically-acceptable diluent or carrier, for use in the production of an pro-apoptotic effect in a warm-blooded animal such as man.

In an additional embodiment, the present invention provides a pharmaceutical composition comprising a compound of formula (I), or a pharmaceutically acceptable salt thereof, and at least one pharmaceutically-acceptable diluent or carrier, for use in the treatment of myeloproliferative disorders, myelodysplastic syndrome, and cancer in a warm-blooded animal such as man.

In an additional embodiment, the present invention provides a pharmaceutical composition comprising a compound of formula (I), or a pharmaceutically acceptable salt thereof, and at least one pharmaceutically-acceptable diluent or carrier, for use in the treatment of chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and cancers selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma, and leukaemia in a warm blooded animal such as man.

In an additional embodiment, the present invention provides a pharmaceutical composition comprising a compound of formula (I), or a pharmaceutically acceptable salt thereof, and at least one pharmaceutically acceptable diluent or carrier, for use in the treatment of myeloma, leukemia, ovarian cancer, breast cancer, and prostate cancer in a warm-blooded animal, such as man.

In an additional embodiment, the present invention provides a pharmaceutical composition comprising a compound of formula (I), or a pharmaceutically acceptable salt thereof, and at least one pharmaceutically-acceptable diluent or carrier, for use in the treatment of cancer, wherein said cancer is selected from oesophageal cancer, myeloma, hepatocellular, pancreatic, cervical cancer, Ewings sarcoma, neuroblastoma, Kaposi's sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, mesothelioma, renal cancer, lymphoma and leukaemia in a warm blooded animal such as man.

In an additional embodiment, the present invention provides a pharmaceutical composition comprising a compound of formula (I), or a pharmaceutically acceptable salt thereof, and at least one pharmaceutically-acceptable diluent or carrier, for use in the production of a JAK inhibitory effect in a warm blooded animal such as man.

In an additional embodiment the present invention provides a compound of formula (I), or a pharmaceutically acceptable salt thereof, for use in the inhibition of Trk activity.

In an additional embodiment the present invention provides a compound of formula (I), or a pharmaceutically acceptable salt thereof, for use in the treatment or prophylaxis of cancer.

In an additional embodiment the present invention provides a compound of the formula (I), or a pharmaceutically acceptable salt thereof, for use in the treatment of cancer in a warm-blooded animal such as man.

In an additional embodiment the present invention provides a compound of the formula (I), or a pharmaceutically acceptable salt thereof, for use in the treatment or prophylaxis of cancers (solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the production of an anti-proliferative effect.

In one embodiment where the inhibition of Trk activity is referred to particularly this refers to the inhibition of Trk A activity.

In another embodiment where the inhibition of Trk activity is referred to particularly this refers to the inhibition of Trk B activity.

Where the treatment (or prophylaxis) of cancer is referred to, particularly it refers to the treatment (or prophylaxis) of mesoblastic nephroma, mesothelioma, acute myeloblastic leukemia, acute lymphocytic leukemia, multiple myeloma, oesophageal cancer, myeloma, hepatocellular, pancreatic, cervical cancer, Ewings sarcoma, neuroblastoma, Kaposi's sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma, leukaemia, tumours of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it refers to hormone refractory prostate cancer.

In a further aspect of the present invention provides a process for preparing a compound of formula (I) or a pharmaceutically acceptable salt thereof which process (wherein variable groups are, unless otherwise specified, as defined in formula (I)) comprises:

Process a) reaction of a pyrimidine of formula (II):

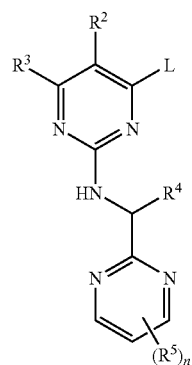

wherein L is a displaceable group; with an pyrazole amine of formula (III):

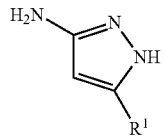

or
Process b) reacting a pyrimidine of formula (IV):

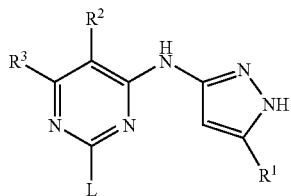

wherein L is a displaceable group; with a compound of formula (V):

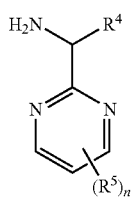

Process c) reacting a compound of formula (VI):

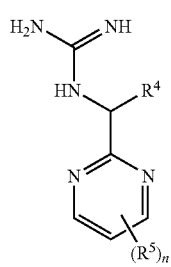

with a compound of formula (VII):

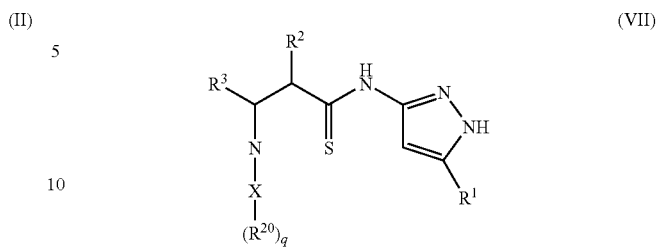

wherein X is an oxygen atom and q is 1; or X is a nitrogen atom and q is 2; and wherein each
$R^{20}$ independently represents a $C_{1-6}$alkyl group; or
Process d) reacting a compound of formula (VIII):

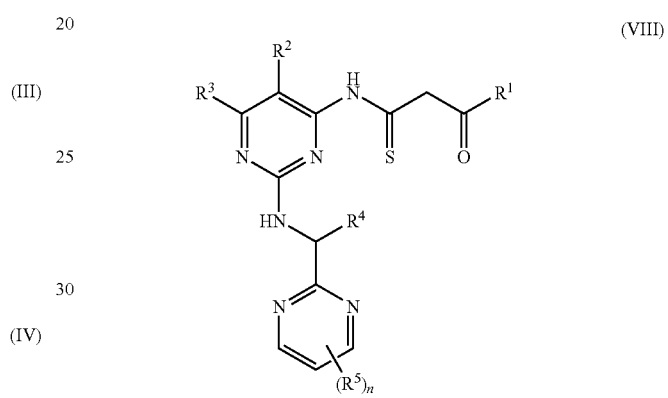

with hydrazine; or
and thereafter if necessary:
i) converting a compound of the formula (I) into another compound of the formula (I);
ii) removing any protecting groups;
iii) forming a pharmaceutically acceptable salt.

L is a displaceable group, suitable values for L are for example, a halo or sulphonyloxy group, for example a chloro, bromo, methanesulphonyloxy or toluene-4-sulphonyloxy group.

Specific reaction conditions for the above reactions are as follows.

Process a) Pyrimidines of formula (II) and pyrazole amine of formula (III) may be reacted together:
a) in the presence of a suitable solvent for example a ketone such as acetone or an alcohol such as ethanol or butanol or an aromatic hydrocarbon such as toluene or N-methyl pyrrolid-2-one, optionally in the presence of a suitable acid for example an inorganic acid such as hydrochloric acid or sulphuric acid, or an organic acid such as acetic acid or formic acid (or a suitable Lewis acid) and at a temperature in the range from 0° C. to reflux, particularly reflux; or
b) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range from 25 to 80° C.

Pyrimidines of the formula (II) may be prepared according to Scheme 1:

Scheme 1

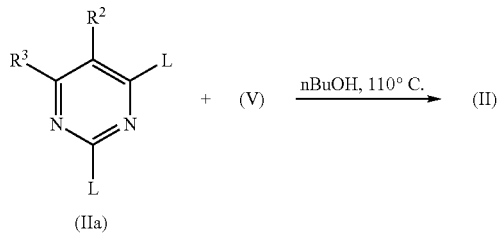

(IIa)

wherein L is a displaceable group as defined herein above.

Pyrazole amines of formula (III) and compounds of formula (IIa) are commercially available compounds, or they are known in the literature, or they are prepared by standard processes known in the art.

Process b) Compounds of formula (IV) and formula (V) may be reacted together under the same conditions as outlined in Process a).

Compounds of the formula (IV) may be prepared according to Scheme 2:

Scheme 2

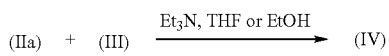

Compounds of the formula (V) are commercially available compounds, or they are known in the literature, or they are prepared by standard processes known in the art.

Process c) may conveniently be carried out in a suitable solvent such as N-methylpyrrolidinone or butanol at a temperature in the range from 100-200° C., in particular in the range from 150-170° C. The reaction is preferably conducted in the presence of a suitable base such as, for example, sodium methoxide or potassium carbonate.

Compounds of the formula (VI) may be prepared according to Scheme 3:

Scheme 3

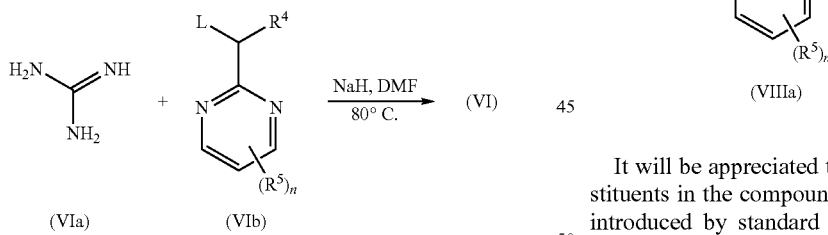

Compounds of the formula (VII) may be prepared according to Scheme 4:

Scheme 4

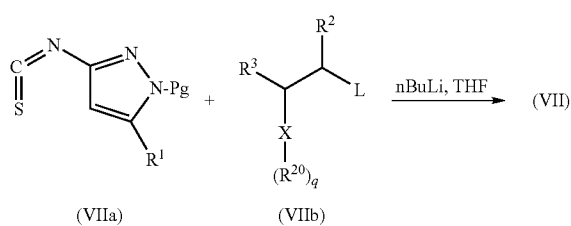

wherein Pg is a suitable nitrogen protecting group. Suitable values for Pg are defined below.

Compounds of the formula (VIa), (VIb), (VIIa) and (VIIb) are commercially available compounds, or they are known in the literature, or they are prepared by standard processes known in the art.

Process d) may be carried out in a suitable solvent, for example, an alcohol such as ethanol or butanol at a temperature in the range from 50-120° C., in particular in the range from 70-100° C.

Compounds of the formula (VIII) may be prepared according to Scheme 5:

Scheme 5

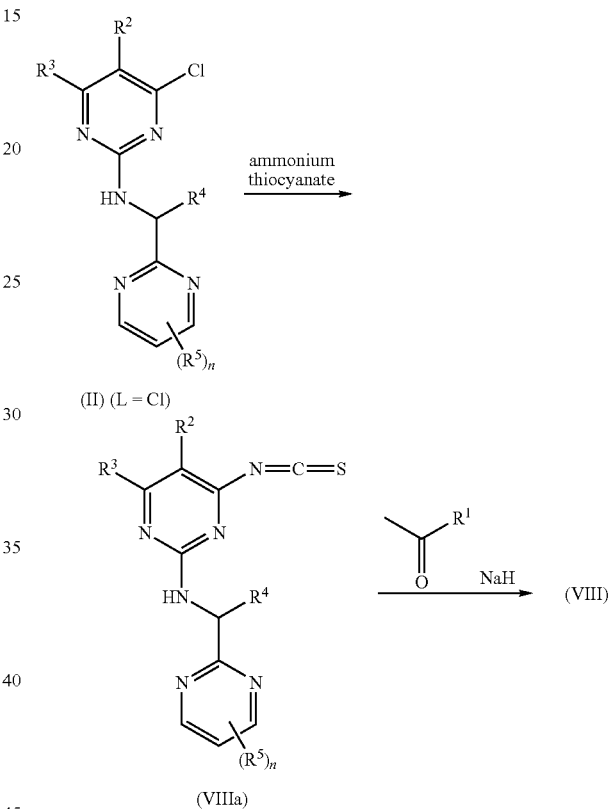

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

DEFINITIONS

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as "propyl" are specific for the straight-chained version only and references to individual branched chain alkyl groups such as "isopropyl" are specific for the branched-chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —CH$_2$— group can optionally be replaced by a —C(O)—, and a ring sulphur atom may be optionally oxidised to form the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are morpholino, piperazinyl and pyrrolidinyl. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —CH$_2$— group can optionally be replaced by a —C(O)—, and a ring sulphur atom may be optionally oxidised to form the S-oxides.

A "3-5-membered heterocyclyl" is a saturated, partially saturated or unsaturated, monocyclic ring containing 3, 4 or 5 atoms of which at least one atom is chosen from nitrogen, sulphur or oxygen, which may, unless otherwise specified, be carbon or nitrogen linked, wherein a —CH$_2$— group can optionally be replaced by a —C(O)—, and a ring sulphur atom may be optionally oxidised to form the S-oxides. Examples and suitable values of the term "3-5-membered heterocyclyl" are pyrrolyl, pyrrolinyl, imidazolyl, thiazolyl and furanyl.

A "carbocyclyl" is a saturated, partially saturated or unsaturated, mono or bicyclic carbon ring that contains 3-12 atoms; wherein a —CH$_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

A "3-5-membered carbocyclyl" is a saturated, partially saturated or unsaturated, monocyclic carbon ring that contains 3, 4 or 5 atoms; wherein a —CH$_2$— group can optionally be replaced by a —C(O)—. Suitable values for "3-5-membered carbocyclyl" include cyclopropyl, cyclobutyl, 1-oxocyclopentyl, cyclopentyl or cyclopentenyl.

The term "$C_{m-n}$" or "$C_{m-n}$group" used alone or as a prefix, refers to any group having m to n carbon atoms.

The term "optionally substituted" refers to either groups, structures, or molecules that are substituted and those that are not substituted.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkoxyimino" include $C_{1-4}$alkoxyimino, $C_{1-3}$alkoxyimino, methoxyimino, ethoxyimino and propoxyimino. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylthio" include methylthio and ethylthio. Examples of "$C_{1-6}$alkylsulphonylamino" include methylsulphonylamino and ethylsulphonylamino. Examples of "$C_{1-6}$alkanoyl" include $C_{1-4}$alkanoyl, propionyl and acetyl. Examples of "N—($C_{1-6}$alkyl)amino" include methylamino and ethylamino. Examples of "N,N—($C_{1-6}$alkyl)$_2$-amino" include di-N-methylamino, di-(N-ethyl)amino and N-ethyl-N-methylamino. Examples of "$C_{2-6}$alkenyl" are vinyl, alkyl and 1-propenyl. Examples of "$C_{2-6}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are N—($C_{1-4}$alkyl)carbamoyl, methylaminocarbonyl and ethylaminocarbonyl. Examples of "N,N—($C_{1-6}$alkyl)$_2$-carbamoyl" are N,N—($C_{1-4}$alkyl)$_2$-carbamoyl, dimethylaminocarbonyl and methylethylaminocarbonyl. Examples of "N—($C_{1-6}$alkyl)-N—($C_{1-6}$alkylsulphonyl)amino" are N-methyl-N-mesylamino and N-ethyl-N-mesylamino. Examples of ($C_{1-6}$alkyl)$_2$N—S(O)$_2$—NH— include (CH$_3$)$_2$N—S(O)$_2$—NH— and (CH$_3$)(C$_2$H$_5$)N—S(O)$_2$—NH—. Examples of ($C_{1-6}$alkyl)NH—S(O)$_2$—NH— include (CH$_3$)NH—S(O)$_2$—NH— and (C$_3$H$_7$)NH—S(O)$_2$—NH—. Examples of ($C_{1-6}$alkyl)$_2$N—S(O)$_2$—N($C_{1-6}$alkyl)- include (CH$_3$)$_2$N—S(O)$_2$—N($C_{1-6}$alkyl) and (CH$_3$)(C$_3$H$_5$)N—S(O)$_2$—N(C$_2$H$_5$)—. Examples of ($C_{1-6}$alkyl)NH—S(O)$_2$—N($C_{1-6}$alkyl)- include (CH$_3$)NH—S(O)$_2$—N(CH$_3$)— and (CH$_3$)NH—S(O)$_2$—N(C$_2$H$_5$). Examples of NH$_2$—S(O)$_2$—N($C_{1-6}$alkyl)- include NH$_2$—S(O)$_2$—N(CH$_3$)— and NH$_2$—S(O)$_2$—N(C$_3$H$_7$).

"RT" or "rt" means room temperature.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It should be noted that the compounds claimed in this invention are capable of existing in different resonance structures and thus the compounds claimed herein include all possible resonance structures, for example optical isomers, diastereoisomers and geometric isomers and all tautomeric forms of the compounds of the formula (I).

It is also to be understood that certain compounds of the formula (I) can exist in solvated as well as unsolvated forms such as, for example, hydrated forms. It is to be understood that the invention encompasses all such solvated forms.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of cancer is an amount sufficient to symptomatically relieve in a warm-blooded animal, particularly a human the symptoms of cancer, to slow the progression of cancer, or to reduce in patients with symptoms of cancer the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quintet, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade]); and the agent anegrilide [Agrylin]; and the agent alpha-interferon;

(ii) cytostatic agents such as antiestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase (MEK1/2) and for example inhibitors of protein kinase B (PKB/Akt), for example inhibitors of Src tyrosine kinase family and/or Abelson (Abl) tyrosine kinase family such as AZD0530 and dasatinib (BMS-354825) and imatinib mesylate (Gleevec); and any agents that modify STAT signalling;

(v) antiangiogenic agents such as those which inhibit the effects of vascular endothelial growth factor, (for example the anti-vascular endothelial cell growth factor antibody bevacizumab [Avastin], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies and approaches using the immunomodulatory drugs thalidomide and lenalidomide [Revlimid]; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

Synthesis

The compounds, or pharmaceutically acceptable salts thereof, of the present invention can be prepared in a number of ways well known to one skilled in the art of organic synthesis. The compounds, or pharmaceutically acceptable salts thereof, of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds, or pharmaceutically acceptable salts thereof, of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in DMSO-d6 unless otherwise stated;

(viii) chemical symbols have their usual meanings;

(ix) solvent ratio was given in volume:volume (v/v) terms.

(x) the following abbreviations have been used:

DMF N,N-dimethylformamide;

THF tetrahydrofuran;

DCM dichloromethane;

DMAP 4-dimethylaminopyridine;

DMSO dimethylsulphoxide;

DIPEA N,N-diisopropylethylamine; and

EtOAc ethyl acetate;

(xi) an ISCO Combiflash refers to flash chromatography on silica gel using Isco Combiflash® separation system: RediSep normal phase flash column, flow rate, 30-40 ml/min.

Example 1

5-Chloro-$N^4$-(5-isopropoxy-1H-pyrazol-3-yl)-$N^2$-[1-(5-fluoropyrimidin-2-yl) ethyl]pyrimidine-2,4-diamine A microwave reaction vessel was charged with 1-(5-fluoropyrimidin-2-yl)ethanamine (Method 1, 0.25 g, 1.77 mmol), 2,5-dichloro-N-(5-isopropoxy-1H-pyrazol-3-yl)pyrimidin-4-amine (Method 2, 0.50 g, 1.77 mmol), and DIPEA (0.30 g, 2.34 mmol). Anhydrous n-BuOH (2 ml) was added, and the tube was sealed and heated in a microwave reactor at 160° C. for 10 hours. The reaction mixture was purified by silica gel chromatography twice (by ISCO Combiflash with gradient EtOAc and DCM) to afford the title compound as a white solid (0.19 g, 27%). LC-MS, 393 (M+1). $^1$H NMR (CDCl$_3$) δ 8.50 (s, 2H), 7.75 (s, 1H), 5.50 (s, 1H), 5.20 (m, 1H), 4.68 (m, 1H), 1.55 (d, 3H), 1.20 (d, 6H).

Example 2

5-Chloro-$N^2$-[(1S)-1-(5-fluoropyrimidin-2-yl)ethyl]-$N^4$-(5-isopropoxy-1H-pyrazol-3-yl) pyrimidine-2,4-diamine

Example 3

5-Chloro-$N^2$-[(1R)-1-(5-fluoropyrimidin-2-yl)ethyl]-$N^4$-(5-isopropoxy-1H-pyrazol-3-yl)pyrimidine-2,4-diamine The title compounds were separated from Example 1 using the chiral HPLC system.
Column and Solvent Conditions:
Column: Chiralpak AD, 250×20 mm, 10µ;
Conditions: 80% hexane, 20% isopropanol, 0.1% diethylamine;
Flow rate: 20 ml/min.
Post purification purity check. The sample purity was checked using the following conditions:
Chiral HPLC using Diode Array
Column: Chiralpak AD, 250×20 mm, 10µ;
Conditions: 80% hexane, 20% isopropanol, 0.1% diethylamine;
Flow rate: 1 ml/min.
The first peak (retention time: 9.21 min, with (−) optical rotation reading) is the S-isomer
The second peak (retention time: 13.54 min, with (+) optical rotation reading) is the R-isomer
Enantiomeric excess for each individual enantiomer (e.e.): >99% calculated using area percent at 254 nm.

Example 2

LC-MS, 393 (M+1). $^1$H NMR (CDCl$_3$) δ 8.50 (s, 2H), 7.75 (s, 1H), 5.50 (s, 1H), 5.20 (m, 1H), 4.68 (m, 1H), 1.55 (d, 3H), 1.20 (d, 6H).

Example 3

LC-MS, 393 (M+1). $^1$H NMR (CDCl$_3$) δ 8.50 (s, 2H), 7.75 (s, 1H), 5.50 (s, 1H), 5.20 (m, 1H), 4.68 (m, 1H), 1.55 (d, 3H), 1.20 (d, 6H).

Example 4

5-Fluoro-$N^2$-[(1S)-1-(5-fluoropyrimidin-2-yl)ethyl]-$N^4$-(5-methyl-1H-pyrazol-3-yl)pyrimidine-2,4-diamine A mixture of (3)-1-(5-fluoropyrimidin-2-yl)ethanamine hydrochloride (Method 7, 95 mg), 2-chloro-5-fluoro-N-(5-methyl-1H-pyrazol-3-yl)pyrimidin-4-amine (Method 8, 114 mg) and DIPEA (0.13 ml) in n-BuOH (2.5 ml) was charged into a microwave reaction vessel. The vessel was sealed and heated in microwave reactor at 180° C. for 6 hours. The solvent was removed under reduced pressure and the residue was purified by Gilson (10-50% MeCN/H$_2$O, 15 min) to give the titled compound as solid (40.7 mg). NMR 11.26 (s, 1H), 8.67-9.18 (m, 3H), 8.22 (s, 1H), 6.04 (s, 1H), 4.86-5.40 (m, 1H), 2.25 (s, 3H), 1.57 (d, 3H); m/z 333.

Example 5

5-Chloro-$N^2$-[(1S)-1-(5-fluoropyrimidin-2-yl)ethyl]-$N^4$-(5-methyl-1H-pyrazol-3-yl)pyrimidine-2,4-diamine A mixture of (5)-1-(5-fluoropyrimidin-2-yl)ethanamine hydrochloride (Method 7, 80 mg), 2,5-dichloro-N-(5-methyl-1H-pyrazol-3-yl)pyrimidin-4-amine (Method 9, 122 mg) and DIPEA (0.134 ml) in n-BuOH (2.5 ml) was charged into a microwave reaction vessel. The vessel was sealed and heated in microwave reactor at 180° C. for 6 hours. The solvent was removed under reduced pressure and the residue was purified by Gilson (10-50% MeCN/H$_2$O, 15 min) to give the titled compound as solid (90 mg). NMR 10.34 (s, 1H), 8.91 (s, 3H), 8.30 (s, 1H), 5.94 (s, 1H), 4.96-5.34 (m, 1H), 2.25 (s, 3H), 1.56 (d, 3H); m/z 350.

Example 6

5-Bromo-$N^2$-[(1S)-1-(5-fluoropyrimidin-2-yl)ethyl]-$N^4$-(5-isopropoxy-1H-pyrazol-3-yl)pyrimidine-2,4-diamine A mixture of 5-bromo-2-chloro-N-(5-isopropoxy-1H-pyrazol-3-yl)pyrimidin-4-amine (Method 13, 150 mg, 0.45 mmol), (S)-1-(5-fluoropyrimidin-2-yl)ethanamine hydrochloride (Method 7, 88 mg, 0.5 mmol) and DIPEA (0.12 ml) in n-BuOH (2 ml) was charged into a microwave reaction vessel. The vessel was sealed and heated in microwave reactor at 165° C. for 4 hours. The solvent was removed under reduced pressure and the residue was purified by flash chromatography on silica gel (20-60% EtOAc in hexanes) to give the titled compound as solid (118 mg, 60%). NMR: 11.98 (s, 1H), 9.36 (s, 1H), 8.82 (s, 2H), 8.10 (s, 1H), 7.96 (s, 1H), 5.56 (s, 1H), 5.13 (s, 1H), 4.66 (m, 1H), 1.48 (m, 3H), 1.26 (m, 6H); m/z 437.

Example 7

5-Chloro-$N^2$-[(1S)-1-(5-fluoropyrimidin-2-yl)ethyl]-10-(5-methoxy-1H-pyrazol-3-yl)pyrimidine-2,4-diamine 2,5-Dichloro-N-(5-methoxy-1H-pyrazol-3-yl)pyrimidin-4-amine (Method 14, 0.25 mmol, 64 mg) and (5)-1-(5-fluoropyrimidin-2-yl)ethanamine hydrochloride (Method 7, 0.25 mmol, 44.4 mg) were dissolved in n-BuOH (0.8 ml) and DIPEA (0.13 mL) was added. The reaction was then stirred at 110° C. overnight. The solvent was evaporated and the remaining material was separated between EtOAc and water, the combined organic extract washed with brine, and dried. Evaporation of the solvent gave a brown oil (59 mg). Purification by Gilson (10-50% MeCN/H$_2$O, 15 minutes) afforded the title compound as a white solid (14.3 mg).
NMR: 9.64 (s, 1H), 8.78 (d, 2H), 8.18 (s, 1H), 7.86 (s, 1H), 5.52 (s, 1H), 4.99-5.15 (m, 1H), 3.65 (s, 3H), 1.43 (d, 3H); m/z 366.

Example 8

5-Chloro-$N^4$-(5-cyclopropyl-1H-pyrazol-3-yl)-$N^2$-[(1S)-1-(5-fluoropyrimidin-2-yl)ethyl]pyrimidine-2,4-diamine A mixture of (S)-1-(5-fluoropyrimidin-2-yl)ethanamine hydrochloride (Method 7, 93 mg), 2,5-dichloro-N-(5-cyclopropyl-1H-pyrazol-3-yl)pyrimidin-4-amine (Method 15, 135 mg) and DIPEA (0.26 ml) in n-BuOH (2.5 ml) was charged into a microwave reaction vessel. The vessel was sealed and heated in microwave reactor at 180° C. for 6 hours. The solvent was removed under reduced pressure and the residue was purified by Gilson (10-50% MeCN/H$_2$O, 15 minutes) to give the titled compound as solid (435 mg). NMR: 10.64 (s, 1H), 8.91 (s, 3H), 8.30 (s, 1H), 5.97 (s, 1H), 5.17 (s, 1H), 1.83-1.97 (m, 1H), 1.56 (d, 3H), 0.93-1.09 (m, 2H), 0.63-0.77 (m, 2H). m/z 413.

Example 9

N$^4$-(5-Cyclopropyl-1H-pyrazol-3-yl)-5-fluoro-N$^2$-[(1S)-1-(5-fluoropyrimidin-2-yl)ethyl]pyrimidine-2,4-diamine A mixture of (S)-1-(5-fluoropyrimidin-2-yl)ethanamine hydrochloride (Method 7, 93 mg), 2-chloro-N-(5-cyclopropyl-1H-pyrazol-3-yl)-5-fluoropyrimidin-4-amine (Method 16, 127 mg) and DIPEA (0.22 ml) in n-BuOH (2.5 ml) was charged into a microwave reaction vessel. The vessel was sealed and heated in microwave reactor at 180° C. for 6 hours. The solvent was removed under reduced pressure and the residue was purified by Gilson (10-50% MeCN/H$_2$O, 15 minutes) to give the titled compound as solid (435 mg). NMR 11.28 (s, 1H), 8.92 (s, 3H), 8.24 (s, 1H), 6.04 (s, 1H), 4.92-5.54 (m, 1H), 1.82-1.98 (m, 1H), 1.56 (d, 3H), 0.94-1.06 (m, 2H), 0.64-0.80 (m, 2H). m/z 395.

Example 10

N-[5-Chloro-2-[(1S)-1-(5-fluoro-pyrimidin-2-yl)-ethylamino]-6-(5-isopropoxy-1H-pyrazol-3-ylamino)-pyrimidin-4-yl]-N-methyl-methanesulfonamide To a solution of N-[2,5-dichloro-6-(5-isopropoxy-1H-pyrazol-3-ylamino)-pyrimidin-4-yl]-N-methyl-methanesulfonamide (Method 18, 191 mg, 0.5 mmol) in n-BuOH (2 ml) was added S-1-(5-fluoro-pyrimidin-2-yl)-ethylamine hydrochloride (Method 7, 172 mg, 1.2 mmol) and ethyldiisopropyl-amine (157 mg). The mixture was heated at 180° C. in microwave for 2 hours. LC/MS showed the completion of the reaction. The solvent was evaporated and the residue was dissolved in DCM, which was then washed by aqueous NaHCO$_3$, dried and concentrated. Flash chromatography was performed with EtOAc/Hex (75%) as eluent. A colourless solid (134 mg) was obtained, yield 56%. NMR (CDCl$_3$) 8.64 (s, 2H), 7.61 (s, 1H), 5.74 (s, 0.6H), 5.42 (s, 0.9H), 5.25 (s, 1H), 4.83 (s, 1H), 3.20 (s, 3H), 3.18 (s, 3H), 1.63 (d, J=6.2 Hz, 3H), 1.40 (m, 6H). MS (ES$^-$) m/z 498.19, 500.14 [M$^-$].

Example 11

N-[5-Fluoro-2-[(1S)-1-(5-fluoro-pyrimidin-2-yl)-ethylamino]-6-(5-isopropoxy-1H-pyrazol-3-ylamino)-pyrimidin-4-yl]-N-methyl-methanesulfonamide To a solution of N-[2-chloro-5-fluoro-6-(5-isopropoxy-1H-pyrazol-3-ylamino)-pyrimidin-4-yl]-N-methyl-methanesulfonamide (Method 20, 210 mg, 0.5 mmol) in n-BuOH (2 ml) was added S-1-(5-fluoro-pyrimidin-2-yl)-ethylamine hydrochloride (Method 7, 197 mg, 1.1 mmol) and ethyldiisopropyl-amine (142 mg). The mixture was heated at 180° C. in microwave for 2 hours. LC/MS showed the completion of the reaction. The solvent was evaporated and the residue was dissolved in DCM, which was then washed by aqueous NaHCO$_3$, dried and concentrated. Flash chromatography was performed with EtOAc/Hex (75%) as eluent. A colourless solid (147 mg) was obtained, yield 55%. NMR (CDCl$_3$) 8.62 (m, 2H), 7.57 (s, 0.8H), 5.38 (s, 0.8H), 5.18 (m, 1H), 4.81 (s, 0.9H), 3.23 (s, 3H), 3.20 (s, 3H), 1.61 (d, J=6.8 Hz, 3H), 1.39 (m, 6H). MS (ES+) m/z 484.32 [MH+]. MS (ES$^-$) m/z 482.18 [M$^-$].

Example 12

6-Chloro-N$^2$-[(1S)-1-(5-fluoropyrimidin-2-yl)ethyl]-N$^4$-(5-methyl-1H-pyrazol-3-yl)pyrimidine-2,4-diamine Following a similar procedure to that of Example 9, the title compound was synthesized from 2,6-dichloro-N-(5-methyl-1H-pyrazol-3-yl)pyrimidin-4-amine (Method 17) and (5)-1-(5-fluoropyrimidin-2-yl)ethanamine hydrochloride (Method 7). m/z 348.

Example 13

N$^2$-[(1S)-1-(5-Fluoropyrimidin-2-yl)ethyl]-N$^4$-(5-methyl-1H-pyrazol-3-yl)-6-morpholin-4-ylpyrimidine-2,4-diamine A mixture of 6-chloro-N$^2$-[(1S)-1-(5-fluoropyrimidin-2-yl)ethyl]-N$^4$-(5-methyl-1H-pyrazol-3-yl)pyrimidine-2,4-diamine (Example 12, 175 mg), morpholine (0.09 ml) and DIPEA (0.13 ml) in n-BuOH (2.5 ml) was heated to 110° C. for 48 hours. The solvent was removed under reduced pressure and the residue was purified by Gilson (5-35% MeCN/H$_2$O, 15 minutes) to give the titled compound as solid (99 mg) $^1$H NMR: 11.19 (s, 1H) 9.28 (s, 1H) 8.74-9.03 (m, 3H) 5.81-5.83 (m, 1H) 5.73 (s, 1H) 4.98-5.24 (m, 2H) 3.58-4.12 (m, 6H) 2.39 (s, 3H) 1.54 (d, 3H); m/z 436.

Example 14

N$^2$-[(1S)-1-(5-fluoropyrimidin-2-yl)ethyl]-5-methyl-N$^4$-(5-methyl-1H-pyrazol-3-yl)pyrimidine-2,4-diamine A microwave reaction vessel was charged with (S)-1-(5-fluoropyrimidin-2-yl)ethanamine (Method 7, 111 mg, 0.63 mmol), 2-chloro-5-methyl-N-(5-methyl-1H-pyrazol-3-yl)pyrimidin-4-amine (Method 22, 0.50 g, 1.77 mmol), and DIPEA (0.225 mL, 1.26 mmol). Anhydrous n-BuOH (2.1 ml) was added, and the tube was sealed and heated in a microwave reactor at 180° C. for 4 hours. The solvent was removed under reduced pressure and the residue was purified by Gilson (5-95% MeCN/H$_2$O, 15 minutes) to give the titled compound as solid (75 mg) $^1$H NMR (300 MHz, DMSO-d6) δ 10.08 (s, 1H) 8.93 (s, 2H) 8.70 (s, 1H) 7.74 (s, 1H) 5.98 (s, 1H) 4.79-5.44 (m, 1H) 2.23 (s, 3H) 2.10 (s, 3H) 1.57 (d, 3H); m/z 330.

Example 15

N$^2$-[(1S)-1-(5-fluoropyrimidin-2-yl)ethyl]-N$^4$-(5-methyl-1H-pyrazol-3-yl)-5-(trifluoromethyl)pyrimidine-2,4-diamine A microwave reaction vessel was charged with (S)-1-(5-fluoropyrimidin-2-yl)ethanamine (Method 7, 111 mg, 0.63 mmol), 2-chloro-N-(5-methyl-1H-pyrazol-3-yl)-5-(trifluoromethyl)pyrimidin-4-amine (Method 23, 0.50 g, 1.77 mmol), and DIPEA (0.225 mL, 1.26 mmol). Anhydrous n-BuOH (2.1 ml) was added, and the tube was sealed and heated in a microwave reactor at 180° C. for 4 hours.) The solvent was removed under reduced pressure and the residue was purified by Gilson (5-95% MeCN/H$_2$O, 15 minutes) to give the titled compound as solid (50 mg) $^1$H NMR (300 MHz, DMSO-d6) δ 8.79 (s, 2H) 8.16 (s, 1H) 8.08 (s, 1H) 5.77 (s, 1H) 5.13 (m, 1H) 2.12 (s, 3H) 1.43 (d, 3H); m/z 383.

Example 16

5-chloro-N$^2$-[(1R)-1-(5-fluoropyrimidin-2-yl)ethyl]-N$^4$-(5-methyl-1H-pyrazol-3-yl)pyrimidine-2,4-diamine A mixture of rac-1-(5-fluoropyrimidin-2-yl)ethanamine hydrochloride (Method 1, 100 mg), 2,5-dichloro-N-(5-methyl-1H-pyrazol-3-yl)pyrimidin-4-amine (Method 9, 200 mg) and DIPEA (0.150 ml) in n-BuOH (2.5 ml) was charged into a microwave reaction vessel. The vessel was sealed and heated in microwave reactor at 180° C. for 6 hours. The solvent was removed under reduced pressure and the residue was purified by Gilson (10-50% MeCN/H$_2$O, 15 min) to give 5-chloro-N$^2$-[1-(5-fluoropyrimidin-2-yl)ethyl]-N$^4$-(5-methyl-1H-pyrazol-3-yl)pyrimidine-2,4-diamine as solid (55 mg). The tile compound was obtained after chiral purification using SFC conditions (Chiralpak AD-H, 20% i-PrOH/80% CO$_2$/0.1% Dimethylethylamine). 1H NMR (300 MHz, DMSO-d6) δ 12.03 (s, 1H) 8.83 (s, 2H) 7.88 (s, 1H) 7.44 (s, 1H) 5.93 (s, 1H) 4.92-5.29 (m, 1H) 2.20 (s, 3H) 1.49 (d, 3H); m/z 350.

Example 17

N-{5-chloro-2-{[(1S)-1-(5-fluoropyrimidin-2-yl)ethyl]amino}-6-[(5-methyl-1H-pyrazol-3-yl)amino]pyrimidin-4-yl}-N,N',N'-trimethylsulfamide A microwave reaction vessel was charged with N-{2,5-dichloro-6-[(5-methyl-1H-pyrazol-3-yl)amino]pyrimidin-4-yl}-N,N',N'-trimethylsulfamide (Method 24, 83.9 mg, 0.221 mmol), (S)-1-(5-fluoropyrimidin-2-yl)ethanamine hydrochloride (Method 7, 78.4 mg, 0.443 mmol), and DIPEA (0.120 ml, 0.682 mmol). Anhydrous n-BuOH (1 ml) was added, and the tube was sealed and heated in a microwave reactor at 160° C. for 2 hours. The reaction mixture was purified by silica gel chromatography (by ISCO Combiflash with gradient EtOAc and hexane) to afford the title compound as a white solid (95.8 mg, 89.6%). LC-MS, 485 (M+1). $^1$H-NMR (DMSO-d6, 400 MHz, 80° C.) δ 11.48-12.40 (br, 1H), 8.77 (s, 1H), 7.85-8.66 (br, 1H), 6.98-7.61 (br, 1H), 6.23 (s, 1H), 5.14-5.11 (m, 1H), 2.93 (s, 3H), 2.83 (s, 6H), 2.21 (s, 3H), 1.53 (d, 3H).

Example 18

N-{5-chloro-2-{[(1S)-1-(5-fluoropyrimidin-2-yl)ethyl]amino}-6-[(5-methoxy-1H-pyrazol-3-yl)amino]pyrimidin-4-yl}-N,N',N'-trimethylsulfamide A microwave reaction vessel was charged with N-{2,5-dichloro-6-[(5-methoxy-1H-pyrazol-3-yl)amino]pyrimidin-4-yl}-N,N',N'-trimethylsulfamide (Method 29, 44.1 mg, 0.112 mmol), (S)-1-(5-fluoropyrimidin-2-yl)ethanamine hydrochloride (Method 7, 39.5 mg, 0.223 mmol), and DIPEA (0.062 ml, 0.352 mmol). Anhydrous n-BuOH (1 ml) was added, and the tube was sealed and heated in a microwave reactor at 160° C. for 2 hours. The reaction mixture was purified by silica gel chromatography (by ISCO Combiflash with gradient EtOAc and hexane) to afford the title compound as a white solid (48.6 mg, 87%). LC-MS, 501 (M+1). $^1$H NMR (DMSO-d6, 400 MHz) δ 12.01 (s, 1H), 9.76 (s, 1H), 8.83 (s, 2H), 8.21 (s, 1H), 5.60 (s, 1H), 5.04-5.06 (m, 1H), 3.76 (s, 3H), 2.80 (s, 3H), 2.70 (s, 6H), 1.59 (d, 3H).

Example 19

N-{5-chloro-2-{[(1S)-1-(5-fluoropyrimidin-2-yl)ethyl]amino}-6-[(5-methoxy-1H-pyrazol-3-yl)amino]pyrimidin-4-yl}-N-methylmethanesulfonamide A microwave reaction vessel was charged with N-{2,5-dichloro-6-[(5-methoxy-1H-pyrazol-3-yl)amino]pyrimidin-4-yl}-N-methylmethanesulfonamide (Method 25, 63.8 mg, 0.174 mmol), (S)-1-(5-fluoropyrimidin-2-yl)ethanamine hydrochloride (Method 7, 61.7 mg, 0.348 mmol), and DIPEA (0.122 ml, 0.693 mmol). Anhydrous n-BuOH (1 ml) was added, and the tube was sealed and heated in a microwave reactor at 160° C. for 2 hours. The reaction mixture was purified by silica gel chromatography (by ISCO Combiflash with gradient EtOAc and hexane) to afford the title compound as a white solid (63.1 mg, 77%). LC-MS: 472 (M+1). $^1$H NMR (DMSO-d6, 400 MHz) δ 11.71 (s, 1H), 9.40 (s, 1H), 8.77 (s, 2H), 7.91 (s, 1H), 5.65 (s, 1H), 5.07-5.10 (m, 1H), 3.79 (s, 3H), 3.01 (s, 6H), 1.54 (d, 3H).

Example 20

N-{2-{[(1S)-1-(5-fluoropyrimidin-2-yl)ethyl]amino}-6-[(5-methyl-1H-pyrazol-3-yl)amino]pyrimidin-4-yl}-N,N',N'-trimethylsulfamide A microwave reaction vessel was charged with N-{2-chloro-6-[(5-methyl-1H-pyrazol-3-yl)amino]pyrimidin-4-yl}-N,N',N'-trimethylsulfamide (Method 30, 51.9 mg, 0.150 mmol), (S)-1-(5-fluoropyrimidin-2-yl)ethanamine hydrochloride (Method 7, 53.3 mg, 0.301 mmol), and DIPEA (0.079 ml, 0.449 mmol). Anhydrous n-BuOH (1 ml) was added, and the tube was sealed and heated in a microwave reactor at 180° C. for 4 hours. The reaction mixture was purified by silica gel chromatography (by ISCO Combiflash with gradient EtOAc and hexanes) to afford the title compound as a white solid (47.4 mg, 70%). LC-MS, 451 (M+1). 1H NMR (DMSO-d6, 400 MHz, 80° C.) δ 11.61 (s, 1H), 8.95 (s, 1H), 8.77 (s, 2H), 5.84-6.89 (m, 3H), 5.17-5.23 (m, 1H), 3.17 (s, 3H), 2.74 (s, 6H), 2.18 (s, 3H), 1.54 (d, 3H).

Example 21

N-{5-fluoro-2-{[(1S)-1-(5-fluoropyrimidin-2-yl)ethyl]amino}-6-[(5-pyrazol-3-yl)amino]pyrimidin-4-yl}-N-methylmethanesulfonamide A microwave reaction vessel was charged with N-{2-chloro-5-fluoro-6-[(5-methyl-1H-pyrazol-3-yl)amino]pyrimidin-4-yl}-N-methylmethanesulfonamide (Method 32, 111 mg, 0.332 mmol), (S)-1-(5-fluoropyrimidin-2-yl)ethanamine hydrochloride (Method 7, 143 mg, 0.668 mmol), and DIEA (0.250 ml, 1.44 mmol). Anhydrous n-BuOH (1 ml) was added, and the tube was sealed and heated in a microwave reactor at 160° C. for 2 hours. The reaction mixture was purified by silica gel chromatography (by ISCO Combiflash with gradient of 0-5% MeOH in DCM with 1% NH$_4$OH) to afford the title compound as a white solid (90 mg, 62%). $^1$H NMR (DMSO, 400 MHz, 80° C.) δ 11.51 (br, 1H), 10.00 (br, 1H), 8.79 (s, 2H), 6.25 (s, 1H), 5.11 (m, 1H), 3.14 (s, 3H), 3.08 (s, 3H), 2.21 (s, 3H), 1.53 (d, 3H); m/z 441.

Example 22

N$^4$-[5-(dimethylamino)-1H-pyrazol-3-yl]-5-fluoro-N$^2$-[(1S)-1-(5-fluoropyrimidin-2-yl)ethyl]pyrimidine-2,4-diamine A microwave reaction vessel was charged with N$^3$-(2-chloro-5-fluoropyrimidin-4-yl)-N$^5$,N$^5$-dimethyl-1H-pyrazole-3,5-diamine (Method 35, 50 mg, 0.2 mmol), (S)-1-(5-fluoropyrimidin-2-yl)ethanamine hydrochloride (Method 7, 50 mg, 0.23 mmol), and DIPEA (0.15 ml, 0.86 mmol) in n-BuOH (1 ml) was heated in a microwave reactor at 160° C. for 2 hours. Solvent was removed. The residue was purified by silica gel chromatography (by ISCO Combiflash with gradient 0-5% Methanol in methylene chloride with 1% NH4OH) to afford the title compound as a white solid (49 mg, 67%). $^1$H NMR (CD$_3$OD, 400 MHz) δ 8.77 (s, 2H), 8.23 (s, 1H), 5.32 (br, 1H), 3.92 (q, 1H), 3.13 (s, 6H), 1.71 (d, 3H); m/z 362

Example 23

5-chloro-N$^4$-[5-(dimethylamino)-1H-pyrazol-3-yl]-N$^2$-[(1S)-1-(5-fluoropyrimidin-2-yl)ethyl]pyrimidine-2,4-diamine A microwave reaction vessel was charged with N$^3$-(2,5-dichloropyrimidin-4-yl)-N$^5$,N$^5$-dimethyl-1H-pyrazole-3,5-diamine (Method 36, 50 mg, 0.2 mmol), (S)-1-(5-fluoropyrimidin-2-yl)ethanamine hydrochloride (Method 7, 50 mg, 0.23 mmol), and DIPEA (0.15 ml, 0.86 mmol) in n-BuOH (1 ml) was heated in a microwave reactor at 160° C. for 2 hours. Solvent was removed. The residue was purified by silica gel chromatography (by ISCO Combiflash with gradient 0-5% methanol in DCM with 1% NH$_4$OH) to afford the title compound as a white solid. $^1$H NMR (CD$_3$OD, 400 MHz) δ 8.77 (s, 2H), 8.26 (br, 1H), 5.35 (br, 1H), 3.49 (q, 1H), 3.11 (s, 6H), 1.72 (d, 3H); m/z 378.

Example 24

5-Nitro-N$^4$-(5-cyclopropyl-1H-pyrazol-3-yl)-N$^2$-[(1S)-1-(5-fluoropyrimidin-2-yl)ethyl]pyrimidine-2,4-diamine A 20 mL round bottom flask was charged with (S)-1-(5-Fluoropyrimidin-2-yl)ethanamine hydrochloride (Method 7, 0.25 g, 1.77 mmol), 2-Chloro-N-(5-cyclopropyl-1H-pyrazol-3-yl)-5-nitropyrimidin-4-amine (Method 37, 0.3 g, 1.0 mmol), and DIEA (0.30 g, 2.34 mmol). Anhydrous n-BuOH (5 mL) was added, and the flask was heated at 60° C. for 4 hours. The reaction mixture was washed with brine (5 mL×3), and the organic layer was dried and concentrated. The resulting residue was separated by silica gel column to afford desired product (0.3 g, 75%). LC-MS, 386 (M+1). $^1$H NMR (DMSO-d6) δ 12.3 (s, 1H), 10.5 (s, 1H), 9.1 (s, 1H), 9.0 (s, 1H), 8.80 (s, 2H), 6.1 (s, 1H), 5.2 (dd, 1H), 2.0 (m, 1H), 1.7 (d, 3H), 1.0 (m, 2H), 0.8 (m, 2H).

Example 25

5-bromo-N$^2$-[(1S)-1-(5-fluoropyrimidin-2-yl)ethyl]-N$^4$-(5-methyl-1H-pyrazol-3-yl)pyrimidine-2,4-diamine To a microwave vial was added (S)-1-(5-fluoropyrimidin-2-yl)ethanamine hydrochloride (Method 7, 369 mg, 2.08 mmol), 5-bromo-2-chloro-N-(5-methyl-1H-pyrazol-3-yl)pyrimidin-4-amine (Method 38, 500 mg, 1.73 mmol), and DIEA (468 mg, 3.8 mmol). Anhydrous n-BuOH (5 mL) was added, and the vial was heated in microwave oven at 165° C. for 5 hours. The reaction mixture was concentrated. The resulting residue was separated by silica gel column to afford desired product (320 mg, 47%). LC-MS, 393 (M+1). $^1$H NMR δ 12.02 (s, 1H), 8.82 (s, 2H), 7.94 (s, 1H), 7.48 (s, 0.55H), 5.90 (s, 0.41H), 5.09 (s, 1H), 2.19 (m, 3H), 1.49 (m, 3H).

Example 26

5-bromo-N$^2$-[(1S)-1-(5-fluoropyrimidin-2-yl)ethyl]-N$^4$-(5-methoxy-1H-pyrazol-3-yl)pyrimidine-2,4-diamine To a microwave vial was added (S)-1-(5-fluoropyrimidin-2-yl)ethanamine hydrochloride (Method 7, 155 mg, 0.77 mmol), 5-bromo-2-chloro-N-(5-methoxy-1H-pyrazol-3-yl)pyrimidin-4-amine (Method 39, 180 mg, 0.59 mmol), and DIEA (181 mg, 1.48 mmol). Anhydrous n-BuOH (2.5 mL) was added, and the vial was heated in microwave oven at 165° C. for 5 hours. The reaction mixture was concentrated. The resulting residue was separated by silica gel column to afford desired product (80 mg, 33%). LC-MS, 409 (M+1). $^1$H NMR δ 12.03 (s, 1H), 9.38 (s, 1H), 8.82 (s, 2H), 7.97-8.12 (m, 2H), 5.60 (s, 1H), 5.13 (s, 1H), 3.75 (m, 3H), 1.49 (m, 3H).

Example 27

5-chloro-N$^2$-[(1S)-1-(5-fluoropyrimidin-2-yl)ethyl]-N$^4$-[5-(2,2,2-trifluoroethoxy)-1H-pyrazol-3-yl]pyrimidine-2,4-diamine To a microwave vial was added (S)-1-(5-fluoropyrimidin-2-yl)ethanamine hydrochloride (Method 7, 81 mg, 0.46 mmol), 2,5-dichloro-N-[5-(2,2,2-trifluoroethoxy)-1H-pyrazol-3-yl]pyrimidin-4-amine (Method 40, 100 mg, 0.31 mmol), and DIEA (110 mg, 0.9 mmol). Anhydrous n-BuOH (2.5 mL) was added, and the vial was heated in microwave oven at 165° C. for 5 hours. The reaction mixture was concentrated. The resulting residue was separated by silica gel column to afford desired product (80 mg, 62%). LC-MS, 433 (M+1). $^1$H NMR δ 12.19 (s, 1H), 9.76 (s, 1H), 8.83 (s, 2H), 7.92-8.10 (m, 2H), 5.67 (s, 1H), 5.13 (s, 1H), 4.75 (m, 2H), 1.49 (m, 3H).

Example 28

6-chloro-N$^2$-[(1S)-1-(5-fluoropyrimidin-2-yl)ethyl]-N$^4$-(5-methoxy-1H-pyrazol-3-yl)pyrimidine-2,4-diamine A mixture of (S)-1-(5-fluoropyrimidin-2-yl)ethanamine hydrochloride (Method 7, 512 mg), 2,6-dichloro-N-(5-methoxy-1H-pyrazol-3-yl)pyrimidin-4-amine (Method 42, 682 mg) and DIPEA (1.16 ml) in n-BuOH (13 ml) was heated at 105° C. over night. The solvent was removed under reduced pressure and the residue was purified by Gilson (10-50% MeCN/H₂O, 15 minutes) to give the titled compound as solid (500 mg). ¹H NMR δ 8.92 (s, 2H) 5.95 (s, 1H) 5.18 (s, 1H) 3.77 (s, 3H) 1.49 (d, 3H); m/z 366.

Example 29

N²-[(1S)-1-(5-fluoropyrimidin-2-yl)ethyl]-N⁴-(5-methoxy-1H-pyrazol-3-yl)-6-morpholin-4-yl)pyrimidine-2,4-diamine A mixture of 6-chloro-N²-[(1S)-1-(5-fluoropyrimidin-2-yl)ethyl]-N⁴-(5-methoxy-1H-pyrazol-3-yl)pyrimidine-2,4-diamine (Example 28, 300 mg), morpholine (0.086 mL) and DIPEA (0.218 ml) in n-BuOH (4 ml) was heated at 120° C. over night in microwave tube. The solvent was removed under reduced pressure and the residue was purified by Gilson (10-50% MeCN/H₂O, 15 minutes) to give the titled compound as solid (174 mg). ¹H NMR δ 11.97 (s, 1H) 9.49 (s, 1H) 8.80 (s, 2H) 7.58 (s, 1H) 4.98-5.20 (m, 3H) 3.72 (s, 3H) 3.53 (bs, 4H) 3.18 (bs, 4H) 1.49 (d, 3H); m/z 416.

Example 30

5,6-dichloro-N²-[(1S)-1-(5-fluoropyrimidin-2-yl)ethyl]-10-(5-methoxy-1H-pyrazol-3-yl)pyrimidine-2,4-diamine A mixture of (S)-1-(5-fluoropyrimidin-2-yl)ethanamine hydrochloride (Method 7, 500 mg), 2,5,6-trichloro-N-(5-methoxy-1H-pyrazol-3-yl)pyrimidin-4-amine (Method 43, 756 mg) and DIPEA (1.14 ml) in n-BuOH (13 ml) was heated at 105° C. for 6 hours. The solvent was removed under reduced pressure and the residue was purified by Gilson (10-50% MeCN/H₂O, 35 minutes) to give the titled compound as solid (210 mg). ¹H NMR δ 9.87 (s, 1H) 8.88 (s, 2H) 8.78 (s, 1H) 8.38 (d, 1H) 5.62 (s, 1H) 5.06-5.17 (m, 1H) 3.77 (s, 3H) 1.49 (d, 3H); m/z 399.

Example 31

5-chloro-N²-[(1S)-1-(5-fluoropyrimidin-2-yl)ethyl]-N⁴-(5-methoxy-1H-pyrazol-3-yl)-6-morpholin-4-ylpyrimidine-2,4-diamine A mixture of 5,6-dichloro-N²-[(1S)-1-(5-fluoropyrimidin-2-yl)ethyl]-N⁴-(5-methoxy-1H-pyrazol-3-yl)pyrimidine-2,4-diamine (Example 30, 100 mg), morpholine (0.026 mL) and DIPEA (0.066 ml) in n-BuOH (2.0 ml) was charged into a microwave reaction vessel. The vessel was sealed and heated at 150° C. for 24 hours. The solvent was removed under reduced pressure and the residue was purified by Gilson 2%-40% MeCN/H₂O, 15 minutes) to give the titled compound as solid (21.8 mg). ¹H NMR δ 11.99 (s, 1H) 9.30 (s, 1H) 8.82 (s, 2H) 7.89 (d, 1H) 5.49 (s, 1H) 4.93-5.14 (m, 1H) 3.75 (s, 3H) 3.44-3.62 (m, 4H) 3.09-3.27 (m, 4H) 1.47 (d, 3H) m/z 450.

Example 32

5-fluoro-N²-[(1S)-1-(5-fluoropyrimidin-2-yl)ethyl]-N⁴-[5-methyl-1H-pyrazol-3-yl)-6-morpholin-4-yl]pyrimidine-2,4-diamine A mixture of (S)-1-(5-fluoropyrimidin-2-yl)ethanamine hydrochloride (Method 7, 141 mg), 2-chloro-5-fluoro-N-(5-methyl-1H-pyrazol-3-yl)-6-morpholin-4-ylpyrimidin-4-amine (Method 44, 313 mg) and DIPEA (0.266 ml) in n-BuOH (5.0 ml) was charged into a microwave reaction vessel. The vessel was sealed and heated in microwave reactor at 180° C. for 9 hours. The solvent was removed under reduced pressure and the residue was purified by Gilson (2-40% MeCN/H₂O, 15 minutes) to give the titled compound as solid (38.4 mg). ¹H NMR δ 8.84 (s, 2H) 4.90-5.02 (m, 1H) 3.38-3.72 (m, 8H) 2.16 (s, 3H) 1.44 (d, 3H); m/z 418.

Example 33

5-chloro-2-{[(1S)-1-(5-fluoropyrimidin-2-yl)ethyl]amino}-6-[(5-methoxy-1H-pyrazol-3-yl)amino]pyrimidine-4-carbonitrile A mixture of 5,6-dichloro-N²-[(1S)-1-(5-fluoropyrimidin-2-yl)ethyl]-N⁴-(5-methoxy-1H-pyrazol-3-yl)pyrimidine-2,4-diamine (Example 30, 100 mg), zinc (17 mg), zinc cyanide (31 mg), DPPF (7 mg) and Pd₂(dba)₃ (12 mg) in DMA (2.0 ml) was degassed and heated at 100° C. for 2 hours. The solution was separated between ethyl acetate and water. Organic solvent was removed under reduced pressure and the residue was purified by Gilson (10-50% MeCN/H₂O, 15 minutes) to give the titled compound as solid (42.5 mg). ¹H NMR δ 10.20 (s, 1H) 8.89 (s, 2H) 8.56 (bs, 1H) 5.63 (s, 1H) 5.03-5.29 (m, 1H) 3.75 (s, 3H) 1.47 (d, 3H); m/z 390.

Example 34

N²-[(1S)-1-(5-fluoropyrimidin-2-yl)ethyl]-N⁴-(5-methoxy-1H-pyrazol-3-yl)-6-(trifluoromethyl)pyrimidine-2,4-diamine A mixture of (S)-1-(5-fluoropyrimidin-2-yl)ethanamine hydrochloride (Method 7, 139 mg), N-(5-methoxy-1H-pyrazol-3-yl)-2-(methylsulfonyl)-6-(trifluoromethyl)pyrimidin-4-amine (Method 45, 265 mg) and DIPEA (0.35 ml) in n-BuOH (5.0 ml) was heated at 90° C. for 6 hours. The solvent was removed under reduced pressure and the residue was purified by Gilson (10-50% MeCN/H₂O, 15 minutes) to give the titled compound as solid (16.3 mg). ¹H NMR δ 12.11 (s, 1H) 10.47 (s, 1H) 8.86 (s, 2H) 8.29 (s, 1H) 6.27 (s, 1H) 5.30 (s, 1H) 5.13-5.25 (m, 1H) 3.77 (s, 3H) 1.51 (d, 3H); m/z 399.

Example 35

5-fluoro-N²-[(1S)-1-(5-fluoropyrimidin-2yl)ethyl]-N⁴-5-methoxy-1H-3-yl-6-morpholin-4-ylpyrimidine-2,4-diamine A mixture of (S)-1-(5-fluoropyrimidin-2-yl)ethanamine hydrochloride (Method 7, 232 mg), 2-chloro-5-fluoro-N-(5-methoxy-1H-pyrazol-3-yl)-6-morpholin-4-ylpyrimidin-4-amine (Method 46, 361 mg) and DIPEA (0.46 ml) in n-BuOH (2.5 ml) was charged into a microwave reaction vessel. The vessel was sealed and heated at 170° C. for 24 hours. The solvent was removed under reduced pressure and the residue was purified by Gilson (2-40% MeCN/H₂O, 15 minutes) to give the titled compound as solid (74.2 mg). ¹H NMR δ 10.07 (s, 1H) 8.86 (s, 2H) 5.48 (s, 1H) 5.00 (m, 1H) 3.86 (s, 3H) 3.38-3.62 (m, 8H) 1.48 (d, 3H); 434.

Example 36

N-{5-chloro-2-{[(1-(5-fluoropyrimidin-2-yl)ethyl]amino}-6-[(5-methyl-1H-pyrazol-3-yl)amino]pyrimidin-4-yl}-N-methylmethanesulfonamide Following a similar procedure to that of Example 21, the title compound was made from N-{2,5-dichloro-6-[(5-methyl-1H-pyrazol-3-yl)amino]pyrimidin-4-yl}-N-methyl-methanesulfonamide (Method 47) and (S)-1-(5-fluoropyrimidin-2-yl)ethanamine hydrochloride (Method 7). $^1$H NMR (DMSO-d6, 400 MHz, 80° C.) δ 10.38 (br, 1H), 9.48 (br, 1H), 8.82 (s, 2H), 6.43 (s, 1H), 4.98 (m, 1H), 3.08 (s, 3H), 2.94 (s, 3H), 2.35 (s, 3H), 1.53 (d, 3H).

Example 37

N-{5-chloro-2-{[(1S)-1-(5-fluoropyrimidin-2-yl)ethyl]amino}-6-[(5-isopropoxy-1H-pyrazol-3-yl)amino]pyrimidin-4-yl}-N,N',N'-trimethylsulfamide Following a similar procedure to that of Example 18, the title compound was made from N-{2,5-dichloro-6-[(5-isopropoxy-1H-pyrazol-3-yl)amino]pyrimidin-4-yl}-N,N',N'-trimethylsulfamide (Method 49) and (S)-1-(5-fluoropyrimidin-2-yl)ethanamine hydrochloride (Method 7). LC-MS, 529 (M+1). $^1$H NMR (CD$_2$Cl$_2$, 400 MHz) δ 11.47 (br, 1H), 8.61 (s, 2H), 7.80 (s, 1H), 6.0-6.40 (br, 1H), 5.44 (s, 1H), 5.23 (m, 1H), 4.75 (s, 1H), 2.02 (s, 3H), 2.92 (s, 6H), 1.62 (s, 3H), 1.35 (s, 6H).

Preparation of Starting Materials

Method 1

1-(5-Fluoropyrimidin-2-yl)ethanamine

A round-bottom flask containing 2-(1-azidoethyl)-5-fluoropyrimidine (Method 3, 0.60 g, 3.59 mmol) was charged with 10% Pd/C (0.191 g) and was evacuated and backfilled with H$_2$ via a filled balloon. MeOH (10 ml) was added, and the mixture was allowed to stir at room temperature for 3 hours. The mixture was filtered through a plug of diatomaceous earth, which was subsequently washed well with MeOH. The filtrates were concentrated to give the title compound as a pale yellow oil (0.50 g, 99%). $^1$H NMR (CDCl$_3$) δ 8.60 (s, 2H), 4.65 (br s 2H), 4.10 (m, 1H), 1.20 (d, 3H).

Method 2

2,5-Dichloro-N-(5-isopropoxy-1H-pyrazol-3-yl)pyrimidin-4-amine

A solution of 2,4,5-trichloropyrimidine (533 mg, 2.93 mmol), 5-isopropoxy-1H-pyrazol-3-amine (413 mg, 2.93 mmol) and triethylamine (0.49 ml) in THF (5 ml) was stirred at room temperature for 10 hours. Solvent was removed and EtOAc was added. The solution was washed with water and dried over anhydrous sodium sulfate and was concentrated to give title compound as a white solid (582 mg, 69%). LC-MS, 246 (M-42); $^1$H NMR (CDCl$_3$) δ 8.19 (s, 1H), 7.80 (s, 1H), 5.79 (s, 1H), 4.65 (m, 1H), 1.30 (d, 6H).

Method 3

2-(1-Azidoethyl)-5-fluoropyrimidine

A round-bottom flask containing 1-(5-fluoropyrimidin-2-yl)ethanol (Method 4, 0.79 g, 5.55 mmol) was charged with triethylamine (0.67 g, 6.66 mmol) and anhydrous DCM (10 ml). The solution was cooled to 0° C., and methanesulfonyl chloride (0.70 g, 4.1 mmol) was added dropwise. The resulting mixture was allowed to stir at room temperature for 2 hours, at which point the volatile components were removed using a rotary evaporator. The residue was dissolved in DMF (15 ml) and treated with sodium azide (0.72 g, 11.1 mmol). The resulting mixture was stirred at room temperature for 60 hours. It was then partitioned between EtOAc and brine. The organic layer was obtained, dried (Na$_2$SO$_4$), and evaporated to dryness. The crude material was purified by silica gel chromatography (by ISCO Combiflash with gradient EtOAc and hexanes) to afford the title compound as a colourless oil (0.60 g, 65% yield over two steps). GC-MS, 167 (M), 138 (M-N$_2$), 125 (M-N$_3$); $^1$H NMR (CDCl$_3$) δ 8.60 (s, 2H), 4.60 (m, 1H), 1.65 (d, 3H).

Method 4

1-(5-Fluoropyrimidin-2-yl)ethanol 1-(5-Fluoropyrimidin-2-yl)ethanone (Method 5, 0.77 g) was dissolved in MeOH (15 ml), and the solution was cooled to 0° C. NaBH$_4$ (0.210 g, 5.55 mmol) was added. The mixture was stirred at room temperature for 1 hour and then partitioned between EtOAc and H$_2$O. The organic extract was washed with brine, dried (Na$_2$SO$_4$), filtered, and concentrated to give the title compound as a yellowish oil (0.79 g, 99%). $^1$H NMR (CDCl$_3$) δ 8.65 (s, 2H), 5.20 (m, 1H), 4.00 (br s, 1H), 1.80 (d, 3H).

Method 5

1-(5-Fluoropyrimidin-2-yl)ethanone

A round-bottom-flask containing 5-fluoropyrimidine-2-carbonitrile (Method 6, 1.50 g, 12.19 mmol) was charged with anhydrous THF (30 ml) under N$_2$. The solution was cooled to 0° C., and a solution of MeMgBr (4.90 ml of a 3.0 M solution in ether, 14.62 mmol) was added dropwise. After 2 hours at 0° C., the reaction mixture was quenched with ice water and extracted with EtOAc. The organic extract was washed with brine, dried over Na$_2$SO$_4$, and evaporated to dryness to give the title compound as an oil (0.778 g, yield 46%). GC-MS, 140 (M); $^1$H NMR (CDCl$_3$) δ 8.65 (s, 2H), 2.65 (s, 2H).

Method 6

5-Fluoropyrimidine-2-carbonitrile

A 10 ml microwave vial was charged with 2-chloro-5-fluoropyrimidine (2.0 g, 15.09 mmol), Pd$_2$(dba)$_3$ (0.549 g, 0.6 mmol), DPPF (0.67 g, 1.21 mmol), zinc cyanide (1.15 g, 9.81 mmol), and zinc dust (0.237 mg, 3.62 mmol). The flask was evacuated and backfilled with N$_2$, and anhydrous dimethylacetamide. The vial was mounted onto a Personal Chemistry microwave reactor and heated at 100° C. for 10 hours. The reaction mixture was diluted with EtOAc and then washed with brine three times. The organic layer was obtained and evaporated to dryness. The dried residue was purified by silica gel chromatography (By ISCO Combiflash with gradient EtOAc and hexanes) to afford the title compound as a creamy solid (1.50 g, 80%). GC-MS: 123 (M); $^1$H NMR (CDCl$_3$) δ 8.80 (s, 2H).

Method 7

(S)-1-(5-Fluoropyrimidin-2-yl)ethanamine hydrochloride

To a solution of (S)-tert-butyl-1-(5-fluoropyrimidin-2-yl)ethylcarbamate (Method 10, 0.21 g, 0.87 mmol) in DCM (5 ml) was added HCl (1.3 ml, 5.2 mmol) in dioxane. The reaction was stirred at room temperature for 3 hours. The solvent was removed give the title compound as white solid (quantitative). MS: Calcd.: 141. Found: [M+H]$^+$ 142.

An alternative process for synthesizing (S)-1-(5-Fluoropyrimidin-2-yl)ethanamine hydrochloride is presented in Methods 50 to 53.

Method 8

2-Chloro-5-fluoro-N-(5-methyl-1H-pyrazol-3-yl)pyrimidin-4-amine

To a solution of 5-methyl-1H-pyrazol-3-amine (612 mg, 6.0 mmol) in absolute EtOH (10 ml) was added triethylamine (1.1 ml) and 2,4-dichloro-5-fluoropyrimidine (1.0 g, 6.0 mmol) and the resulting solution was aged at room temperature for 12 hours. The mixture was partitioned between EtOAc and water. The organic layer was washed with brine and dried. The solvents were removed under reduced pressure to give the title compound as a solid (679 mg). m/z: 228.

Method 9

2,5-Dichloro-N-(5-methyl-1H-pyrazol-3-yl)pyrimidin-4-amine

To a solution of 5-methyl-1H-pyrazol-3-amine (2.78 g, 27.3 mmol) in absolute EtOH (30 ml) was added triethylamine (5 ml) and 2,4,5-trichloropyrimidine (5.0 g, 27.3 mmol) and the resulting solution was aged at room temperature for 12 hours. The mixture was partitioned between EtOAc and H$_2$O, the organic layer was washed with brine and dried. The solvents were removed under reduced pressure to give the title compound (4.1 g). m/z: 245.

Method 10

(S)-tert-butyl-1-(5-Fluoropyrimidin-2-yl)ethylcarbamate (S)—N-(1-(5-Fluoropyrimidin-2-yl)ethyl)acetamide (Method 11, 0.20 g, 1.09 mmol), DMAP (0.027 g, 0.22 mmol) and di-tert-butyl-dicarbonate (0.60 g, 2.73 mmol) in THF (10 ml) was stirred at 50° C. for 40 hours. After cooling to room temperature, lithium hydroxide monohydrate (0.094 g, 2.24 mmol) and water (10 ml) was added. The reaction was stirred at room temperature for 9 hours. Ether (30 ml) was added, organic layer was separated, washed with brine (20 ml) and dried over sodium sulfate. After removal of solvent, the resulted residue was purified by column chromatography (Hex-EtOAc=5:1) to give the title compound as a pale yellow oil (0.21 g, 80%). NMR (400 MHz) 8.84 (s, 2H), 7.24 (d, J=7.6 Hz, 1H), 4.74 (m, 1H), 1.35 (s, 12H). MS: Calcd.: 241. Found: [M+H]$^+$ 242.

Method 11

(S)—N-(1-(5-Fluoropyrimidin-2-yl)ethyl)acetamide

N-(1-(5-Fluoropyrimidin-2-yl)vinyl)acetamide (Method 12, 0.10 g, 0.55 mmol) in MeOH (5 ml) under N$_2$ was added (+)-1,2-bis((2S,5S)-2,5-diethylphospholano)benzene (cyclooctadiene)rhodium(I) trifluoromethanesulfonate (0.04 g, 0.0055 mmol). The solution was transferred to a high pressure bomb and charged 150 psi H$_2$. The reaction was stirred at room temperature for 4 hours. The solvent was removed and the resulted residue was purified by column chromatography (EtOAc) to give the title compound as a white solid (0.096 g, 95%). $^1$H NMR (400 MHz) 8.84 (d, J=0.8 Hz, 2H), 8.34 (d, J=7.6 Hz, 1H), 5.00 (m, 1H), 1.84 (s, 3H), 1.37 (d, J=6.8 Hz, 3H). MS: Calcd.: 183. Found: [M+H]$^+$ 184. Enantiomeric excess determined by HPLC (Chiralpak IA; 95:5 CO$_2$/MeOH), >99% ee.

Method 12

N-(1-(5-Fluoropyrimidin-2-yl)vinyl)acetamide

5-Fluoropyrimidine-2-carbonitrile (Method 6, 1.0 g, 8.1 mmol) in TI-IF (10 ml) was added a solution of MeMgBr (3.3 ml, 9.75 mmol) in ether drop wise at 0° C. After addition, the reaction was warmed to room temperature, stirred at room temperature for 1 hour and then diluted with DCM (10 ml). Acetic anhydride (1.23 ml, 13.0 mmol) was added in one portion. The reaction was stirred at room temperature for 1 hour and 40° C. for 1 hour. Saturated sodium bicarbonate solution (10 ml) was added and extracted with EtOAc (2×20 ml). The combined organic was dried over sodium sulfate. After removal of solvent, the resulted residue was purified by column chromatography (hexane-EtOAc=2.5:1) to give the title compound as a white solid (0.38 g, 26%). $^1$H NMR (400 MHz) 9.34 (s, 1H), 8.95 (s, 2H), 6.25 (s, 1H), 6.03 (s, 1H), 2.11 (s, 3H). MS: Calcd.: 181. Found: [M+H]$^+$ 182.

Method 13

5-Bromo-2-chloro-N-(5-isopropoxy-1H-pyrazol-3-yl)pyrimidin-4-amine

To a solution of 5-isopropoxy-1H-pyrazol-3-amine (11.6 g, 82.1 mmol) in THF (85 ml) was added DIPEA (16 ml) and 2,4-dichloro-5-bromopyrimidine (17 g, 74.6 mmol) and the resulting solution was aged at 40° C. for 16 hours. The mixture was partitioned between EtOAc and H$_2$O, the organic layer was washed with brine and dried. The solvents were removed under reduced pressure and column chromatography gave the title compound as a solid. m/z: 332.

Method 14

2,5-Dichloro-N-(5-methoxy-1H-pyrazol-3-yl)pyrimidin-4-amine

To a solution of 5-methoxy-1H-pyrazol-3-amine (890 mg, 7.8 mmol) in absolute EtOH (20 ml) was added triethylamine (3.3 ml, 23.6 mmol) and 2,4,5-trichloropyrimidine (1.4 g, 7.8 mmol) and the resulting solution was aged at room temperature for 12 hours. The mixture was partitioned between EtOAc and H$_2$O, the organic layer was washed with brine and dried. The solvents were removed under reduced pressure to give the title compound as an oil which crystallized upon standing (1.8 g). m/z: 261.

Method 15-17

The following compounds were prepared by the procedure of Method 14, using the appropriate starting material.

| Meth | Compound | m/z | SM |
|---|---|---|---|
| 15 | 2,5-Dichloro-N-(5-cyclopropyl-1H-pyrazol-3-yl)pyrimidin-4-amine | 271 | 5-cyclopropyl-1H-pyrazol-3-amine and 2,4,5-trichloropyrimidine |

-continued

| Meth | Compound | m/z | SM |
|---|---|---|---|
| 16 | 2-Chloro-N-(5-cyclopropyl-1H-pyrazol-3-yl)-5-fluoropyrimidin-4-amine | 254 | 5-cyclopropyl-1H-pyrazol-3-amine and 2,4-dichloro-5-fluoropyrimidine |
| 17 | 2,6-Dichloro-N-(5-methyl-1H-pyrazol-3-yl)pyrimidin-4-amine | 245 | 5-methyl-1H-pyrazol-3-amine and 2,4,6-trichloropyrimidine |

Method 18

N-[2,5-Dichloro-6-(5-isopropoxy-1H-pyrazol-3-ylamino)-pyrimidin-4-yl]-N-methyl-methanesulfonamide To a solution of N-methyl-N-(2,5,6-trichloro-pyrimidin-4-yl)-methanesulfonamide (Method 19, 1.236 g, 4.3 mmol) in n-BuOH (8 ml) was added 5-isopropoxy-1H-pyrazol-3-ylamine (601 mg, 4.3 mmol) and ethyl-diisopropyl-amine (556 mg). The mixture was heated at 70° C. overnight. LC/MS showed the completion of the reaction. The solvent was evaporated and the residue was dissolved in DCM, which was then washed by aqueous $NaHCO_3$, dried and concentrated. Flash chromatography was performed with EtOAc/Hex (50%) as eluent. A colourless solid (669 mg) was obtained, yield 39%. NMR ($CDCl_3$) 8.06 (s, 1H), 5.78 (s, 1H), 4.61 (m, 1H), 3.21 (s, 3H), 3.16 (s, 3H), 1.32 (d, J=6.0 Hz, 6H). MS (ES+) m/z 395.2, 397.1 [MH+]. MS (ES) m/z 393.1, 395.0 [M−].

Method 19

N-Methyl-N-(2,5,6-trichloro-pyrimidin-4-yl)-methanesulfonamide

To N-Methyl methanesulfonate (954 mg, 8.7 mmol) in THF (20 ml) was added NaH (367 mg, 9.2 mmol, 60% in mineral oil). This was stirred for 10 min at room temperature and then added to the solution of 2,4,5,6-tetrachloro-pyrimidine (1.904 g, 8.7 mol) in THF (10 ml) at 0° C. The reaction mixture was stirred at 0° C. for 3 hours. LC/MS showed the completion of the reaction. The solvent was evaporated and the residue was dissolved in DCM, which was then washed by aqueous $NaHCO_3$, dried and concentrated. Flash chromatography was performed with EtOAc/Hex (25%) as eluent. A colourless solid (1.236 g) was obtained, yield 49%. NMR (400 MHz, $CDCl_3$) 3.30 (s, 3H), 3.32 (s, 3H). $^{13}$C-NMR (400 MHz, $CDCl_3$) 162.2, 161.2, 156.0, 124.7, 39.5, 37.1. MS (ES+) m/z 289.83, 291.82 [MH+].

Method 20

N-[2-Chloro-5-fluoro-6-(5-isopropoxy-1H-pyrazol-3-ylamino)-pyrimidin-4-yl]-N-methyl-methanesulfonamide To a solution of N-(2,6-dichloro-5-fluoro-pyrimidin-4-yl)-N-methyl-methanesulfonamide (Method 21, 440 mg, 1.6 mmol) in n-BuOH (3 ml) was added 5-isopropoxy-1H-pyrazol-3-ylamine (227 mg, 1.6 mmol) and DIPEA (207 mg). The mixture was heated at 70° C. overnight. LC/MS showed the completion of the reaction. The solvent was evaporated and the residue was dissolved in DCM, which was then washed by aqueous $NaHCO_3$, dried and concentrated. Flash chromatography was performed with EtOAc/Hex (50%) as eluent. A colourless solid (280 mg) was obtained, yield 46%. $^1$H-NMR (300 MHz, $CD_3OD$) 5.84 (s, 0.8H), 4.61 (m, 1H), 3.32 (s, 3H), 3.27 (s, 3H), 1.36 (d, J=6.0; 6H). MS (ES+) m/z 378.86, 380.86 [MH+]. MS (ES−) m/z 376.88, 378.87 [M−].

Method 21

N-(2,6-Dichloro-5-fluoro-pyrimidin-4-yl)-N-methyl-methanesulfonamide

To N-methyl methanesulfonate (546 mg, 5 mmol) in THF (20 ml) was added NaH (220 mg, 5.5 mmol, 60% in mineral oil). This was stirred for 10 minutes at room temperature and then added to the solution of 2,4,6-trichloro-5-fluoro-pyrimidine (1.007 g, 5 mol) in THF (5 ml) at 0° C. The reaction mixture was stirred at 0° C. for 3 hours. LC/MS showed the completion of the reaction. The solvent was evaporated and the residue was dissolved in DCM, which was then washed by aqueous $NaHCO_3$, dried and concentrated. Flash chromatography was performed with EtOAc/Hex (25%) as eluent. A colourless solid (986 mg) was obtained, yield 72%. NMR ($CDCl_3$) 3.45 (d, J=1.9 Hz, 3H), 3.37 (s, 3H). MS (ES−) m/z 274.0, 276.0 [M−].

Method 22

2-Chloro-5-methyl-N-(5-methyl-1H-pyrazol-3-yl)pyrimidin-4-amine

To a solution of 2,4-dichloro-5-methylpyrimidine (1.25 g, 7.8 mmol) in EtOH (30 ml) was added 5-methyl-1H-pyrazol-3-ylamine (756 mg, 7.8 mmol) and DIPEA (2.8 mL). The mixture was heated at 70° C. overnight. LC/MS showed the completion of the reaction. The title compound was obtained by filtration under vacuum as a white solid (700 mg). m/z 224.

Method 23

2-Chloro-N-(5-methyl-1H-pyrazol-3-yl)-5-(trifluoromethyl)pyrimidin-4-amine

To a solution of 2,4-dichloro-5-trifluoromethylpyrimidine (1.27 g, 5.8 mmol) in MeCN (20 ml) was added 5-methyl-1H-pyrazol-3-ylamine (568 mg, 5.8 mmol) and $Et_3N$ (1.6 mL). The mixture was stirred at ambient temperature overnight. LC/MS showed the completion of the reaction. Evaporation of the solvent afforded yellow oil that was purified by Gilson (5-95% MeCN/$H_2O$, 15 minutes) to give the titled compound as solid (300 mg). m/z 278.

Method 24

N-{2,5-Dichloro-6-[(5-methyl-1H-pyrazol-3-yl)amino]pyrimidin-4-yl}-N,N',N'-trimethylsulfamide To a solution of N,N,N'-trimethyl-N'-(2,5,6-trichloropyrimidin-4-yl)sulfamide (Method 26, 0.505 g, 1.59 mmol) in n-BuOH (3 ml) was added 5-methyl-1H-pyrazol-3-amine (159 mg, 1.59 mmol, 97% purity) and DIPEA (0.419 mL, 2.38 mmol). The mixture was heated at 50° C. overnight. LC/MS showed the completion of the reaction. The solvent was evaporated and the residue was partitioned between DCM and $H_2O$. Then the organic layer was dried over $Na_2SO_4$, filtered to remove solid, then concentrated in vacuo. The residue was purified by silica gel chromatography (by ISCO Combiflash with gradient EtOAc and hexane) to afford the title compound as a light yellow solid (453 mg, 75%). LC-MS, 380 (M+1). NMR (DMSO, 400 MHz) δ 12.33 (s, 1H), 9.82 (s, 1H), 6.24 (s, 1H), 3.08 (s, 3H), 2.91 (s, 6H), 2.25 (s, 3H).

Method 25

The following compound was prepared by the procedure of Method 24, using the appropriate starting material.

| Meth | Compound | m/z | SM | NMR |
|---|---|---|---|---|
| 25 | N-{2,5-dichloro-6-[(5-methoxy-1H-pyrazol-3-yl)amino]pyrimidin-4-yl}-N-methylmethanesulfonamide | 367 | 5-methoxy-1H-pyrazol-3-amine and N-methyl-N-(2,5,6-trichloropyrimidin-4-yl)methanesulfonamide | $^1$H (DMSO-d6, 400 MHz) 11.26 (s, 1H), 9.91 (s, 1H), 5.81 (s, 1H), 3.81 (s, 3H), 3.28 (s, 3H), 3.19 (s, 3H). |

Method 26

N,N,N'-Trimethyl-N'-(2,5,6-trichloropyrimidin-4-yl)sulfamide

To a solution of NaH (343 mg, 8.58 mmol, 0% in mineral oil) in anhydrous DMF (2 mL), N,N,N'-trimethylsulfamide (Method 28, 492 mg, 3.56 mmol) in DMF (2 ml) was added. This reaction mixture was stirred for 30 min at room temperature and then added to the solution of 2,4,5,6-tetrachloropyrimidine (726 mg, 3.26 mmol) in THF (30 ml) at 0° C. The reaction mixture was stirred from 0° C. to room temperature overnight. The solvent was evaporated and the residue was dissolved in DCM, which was then washed by aqueous NH$_4$Cl, dried and concentrated. Flash chromatography was performed with EtOAc/Hex (10%) as eluent. A white solid (553 mg) was obtained, yield 53%. NMR (400 MHz, DMSO) δ 3.18 (s, 3H), 2.93 (s, 6H).

Method 27

The following compound was prepared by the procedure of Method 26, using the appropriate starting material.

| Meth | Compound | m/z | SM | NMR |
|---|---|---|---|---|
| 27 | N-(2,6-dichloropyrimidin-4-yl)-N,N',N'-trimethylsulfamide | 367 | N,N,N'-trimethylsulfamide and 2,4,6-trichloropyrimidine | $^1$H (400 MHz, DMSO) 3.43 (s, 3H), 2.90 (s, 6H). |

Method 28

N,N,N'-Trimethylsulfamide

To a solution of dimethylsulfamoyl chloride (1.49 mL, 13.8 mmol) in DCM (2.0 mL) and K$_2$CO$_3$ (1.24 g, 8.9 mmol), Methylamine (16 mL, 32 mmol, 2M in THF) was added at 0° C. slowly. The reaction mixture was stirred at 0° C. for 1 hr, then warm up to room temperature for another 1 hr. The solvent was removed in vacuo, then anhydrous DCM (30 mL) was added, filtered to remove solid, and then yellow liquid product (1.84 g, 97% yield) was obtained by removing the solvent. NMR (400 MHz, CDCl$_3$) δ 4.40 (s, 1H), 2.74 (s, 6H), 1.70 (s, 3H).

Method 29

N-{2,5-Dichloro-6-[(5-methoxy-1H-pyrazol-3-yl)amino]pyrimidin-4-yl}-N',N'-trimethylsulfamide To a solution of N,N,N'-trimethyl-N'-(2,5,6-trichloropyrimidin-4-yl)sulfamide (Method 26, 318 mg, 1.0 mmol) in n-BuOH (1 ml) was added 5-methoxy-1H-pyrazol-3-amine (102 mg) and DIPEA (0.240 mL, 1.36 mmol). The mixture was heated at 50° C. overnight. The solvent was evaporated and the residue was partitioned between DCM and H$_2$O. Then the organic layer was dried over Na$_2$SO$_4$, filtered to remove solid, then concentrated in vacuo. The residue was purified by silica gel chromatography (by ISCO Combiflash with gradient EtOAc and hexane) to afford the title compound as a dry film (123 mg, 34%). LC-MS, 396 (M+1). NMR (DMSO, 400 MHz) δ 9.74 (s, 1H), 5.81 (s, 1H), 3.81 (s, 3H), 3.12 (s, 3H), 2.93 (s, 6H).

Method 30

N-{2-Chloro-6-[(5-methyl-1H-pyrazol-3-yl)amino]pyrimidin-4-yl}-N,N',N'-trimethylsulfamide To a solution of N-(2,6-dichloropyrimidin-4-yl)-N,N',N'-trimethylsulfamide (Method 27, 1.72 g, 6.05 mmol) in n-BuOH (6 ml) was added 5-methyl-1H-pyrazol-3-amine (0.605 g, 6.05 mmol) and DIPEA (1.6 mL, 9.09 mmol). The mixture was heated at 70° C. overnight. The reaction mixture was filtered; the solid was washed by MeOH three times to give pure white solid. (0.205 g, 9.7% yield). LC-MS, 346 (M+1). NMR (DMSO-d6, 400 MHz, 80° C.) δ 11.89 (s, 1H), 9.82 (s, 1H), 7.22 (s, 1H), 5.97 (s, 1H), 3.32 (s, 3H), 2.87 (s, 6H), 2.21 (s, 3H).

Method 31

N-(2,6-Dichloro-5-fluoropyrimidin-4-yl)-N-methylmethanesulfonamide

To a solution of NaH (60% in mineral oil, 176 mg, 8.58 mmol) in anhydrous DMF (2 mL), N-methylmethanesulfonamide (436 mg, 4.0 mmol) in DMF (2 ml) was added. This reaction mixture was stirred for 30 min at room temperature and then added dropwise to the solution of 2,4,6-trichloro-5-fluoropyrimidine (804 mg, 4.0 mmol) in THF (30 ml) at 0° C. The reaction mixture was stirred from 0° C. to room temperature overnight. The solvent was evaporated and the residue was purified by silica gel chromatography (by ISCO Combiflash with gradient 0-30% ethyl acetate in Hexane with 1%

TEA. A white solid (700 mg) was obtained, yield 64%. NMR (400 MHz, DMSO) δ3.38 (s, 3H), 3.31 (s, 3H).

Method 32

N-{2-Chloro-5-fluoro-6-[(5-methyl-1H-pyrazol-3-yl)amino]pyrimidin-4-yl}-N-methylmethanesulfonamide To a solution of N-(2,6-dichloro-5-fluoropyrimidin-4-yl)-N-methylmethanesulfonamide (Method 31, 914 mg, 3.35 mmol) in n-BuOH (3 ml) was added 5-methyl-1H-pyrazol-3-amine (351 mg, 3.62 mmol, 97% purity) and DIPEA (1.2 ml, 6.9 mmol). The mixture was heated at 50° C. overnight. LC/MS showed the completion of the reaction. The solvent was evaporated and the residue was purified by silica gel chromatography (by ISCO Combiflash with gradient 0-5% methanol in DCM with 1% NH$_4$OH) to afford the title compound as a light yellow solid (1.06 g, 95%). LC-MS, 335 (M+1). NMR (DMSO-d6, 400 MHz) δ12.27 (s, 1H), 10.53 (s, 1H), 6.32 (s, 1H), 3.27 (s, 3H), 3.20 (s, 3H), 2.25 (s, 3H).

Method 33

(2E or Z)-3-(Dimethylamino)-3-(methylthio)acrylonitrile

Acetonitrile (12 ml, 228 mmol) in THF (100 ml) was cooled at −78° C., Butyllithium (2.5M in Hexane, 92 ml, 230 mmol) was added dropwise trough an addition funnel. The reaction was stirred for additional 30 minutes. Methyl dimethyldithiocarbamate (Method 41, 14.09 g, 104 mmol) was added in one portion as solid under nitrogen flow. It was stirred at 78° C. for 30 minutes and room temperature 6 hours. The reaction was then cooled into an ice-bath. Methyl iodide (10 ml, 125 mmol) was added to the reaction through a syringe. The reaction was allowed to warm to room temperature and was stirred at room temperature overnight. Ethyl acetate (200 ml) was added to the reaction, and the reaction was washed with water (2×100 ml). The organic phase was combined and concentrated down, The residue was purified by silica gel chromatography (by ISCO Combiflash with gradient 0-20% ethyl acetate in hexane) to afford the title compound as a white solid (10.5 g, 71%) as a mixture of EZ isomers in the form of brownish liquid. NMR (major isomer) (CDCl$_3$, 400 MHz) δ4.08 (s, 1H), 3.00 (s, 6H), 2.39 (s, 3H).

Method 34

N$^5$,N$^5$-Dimethyl-1H-pyrazole-3,5-diamine

A mixture of (2E or Z)-3-(dimethylamino)-3-(methylthio)acrylonitrile (Method 33, 9.525 g, 67 mmol) and hydrazine hydrate (10.06 g, 201 mmol) in ethanol (70 ml) was heated at 85° C. overnight. Solvent was removed. The residue was purified by silica gel column chromatography (by ISCO Combiflash with a gradient of 0-10% methanol in methylenechloride with 1% NH4OH). 5.8 g (69%) product as obtained brownish thick oil. LC-MS, 127 (M+1). NMR (DMSO, 400 MHz) δ9.51 (br, 1H), 4.67 (s, 1H), 2.62 (s, 6H).

Method 35

N$^3$-(2-Chloro-5-fluoropyrimidin-4-yl)-N$^5$,N$^5$-dimethyl-1H-pyrazole-3,5-diamine 2,4-dichloro-5-fluoropyrimidine (166 mg, 1 mmol), N$^5$,N$^5$-dimethyl-1H-pyrazole-3,5-diamine (Method 34, 150 mg, 1.2 mmol), and DIEA (0.35 ml, 2 mmol) in ethanol (3 ml) was heated at 55° C. overnight. Solvent was removed, and the residue was purified by silica gel chromatography (by ISCO Combiflash with a gradient of 0-5% methanol in methylene chloride with 1% NH4OH). 100 mg product was obtained as a white solid (40%). MS: 257 (M+1); NMR (DMSO-d6, 400 MHz, 80° C.) δ11.60 (br, 1H), 10.26 (br, 1H), 8.23 (s, 1H), 5.73 (s, 1H), 2.76 (s, 6H).

Method 36

The following compound was prepared by the procedure of Method 26, using the appropriate starting material.

| Meth | Compound | m/z | SM | NMR |
|---|---|---|---|---|
| 36 | N$^3$-(2,5-dichloropyrimidin-4-yl)-N$^5$,N$^5$-dimethyl-1H-pyrazole-3,5-diamine | 273 | N$^5$,N$^5$-dimethyl-1H-pyrazole-3,5-diamine and 2,4,5-trichloropyrimidine | $^1$H (DMSO, 400 MHz, 80° C.) δ11.67 (br, 1H), 9.51 (br, 1H), 8.34 (s, 1H), 5.68 (s, 1H), 2.76 (s, 6H). |

Method 37

2-Chloro-N-(5-cyclopropyl-1H-pyrazol-3-yl)-5-nitropyrimidin-4-amine

To a solution of 2,4-dichloro-5-nitropyrimidine (3.0 g, 15 mmol) and DIEA (2.4 g, 18.5 mmol) in n-BuOH (30 ml) was slowly added 5-cyclopropyl-1H-pyrazol-3-amine (2.0 g, 16.2 mmol) at 25° C. The resulting solution was stirred at 25° C. for 5 minutes and concentrated to dryness to give the title compound (3.1 g). NMR (CDCl$_3$) 0.80 (m, 2H), 1.05 (m, 2H), 6.60 (s, 1H), 9.20 (s, 1H), 9.70 (br s, 1H), 10.40 (br s, 1H).

Method 38

5-Bromo-2-chloro-N-(5-methyl-1H-pyrazol-3-yl)pyrimidin-4-amine

To a solution of 5-bromo-2,4-dichloropyrimidine (1.29 g, 5.66 mmol) in EtOH (15 ml) at room temperature was added a solution of 5-methyl-1H-pyrazol-3-amine (549 mg, 5.66 mmol) in EtOH (3 ml) and triethylamine (628 mg, 6.22 mmol) and the reaction mixture was stirred at room temperature overnight. The suspension was filtered and washed with water and dried to give the desired product as a white solid (1.27 g, 78%). NMR (CDCl$_3$) 2.24 (s, 3H), 6.24 (s, 1H), 8.41 (s, 1H), 9.29 (s, 1H), 12.32 (s, 1H).

Method 39

5-Bromo-2-chloro-N-(5-methoxy-1H-pyrazol-3-yl) pyrimidin-4-amine

To a solution of 5-bromo-2,4-dichloropyrimidine (1.20 g, 5.26 mmol) in THF (10 ml) at room temperature was added 5-methoxy-1H-pyrazol-3-amine (594 mg, 5.26 mmol) and triethylamine (685 mg, 6.3 mmol) and the reaction mixture was stirred at 40° C. overnight. The suspension was filtered and washed with water and dried to give the desired product as a white solid. MS: 305 (M+1).

Method 40

2,5-Dichloro-N-[5-(2,2,2-trifluoroethoxy)-1H-pyrazol-3-yl]pyrimidin-4-amine

To a solution of 2,4,5-trichloropyrimidine (1.00 g, 5.45 mmol) in THF (10 ml) at room temperature was added 5-(2,2,2-trifluoroethoxy)-1H-pyrazol-3-amine (986 mg, 5.45 mmol) and triethylamine (606 mg, 6.0 mmol) and the reaction mixture was stirred at 40° C. overnight. The suspension was filtered and washed with water and dried to give the desired product as a white solid. MS: 328 (M+1).

Method 41

Methyl Dimethyldithiocarbamate

Dimethylamine (2M in THF, 60 ml, 120 mmol) was cooled into an ice-bath. Carbon dioxide (6 ml, 100 mmol) was added portionwise, followed by the addition of NaOH (4.8 g)/H$_2$O (40 mL). The reaction was stirred at ice-bath for 30 minutes and room temperature for 2 hours. The reaction was then cooled to ice-bath, and methyl iodide (7.5 ml, 120 mmol) was added slowly through a syringe. The reaction was stirred at ice-bath for 1 h, and room temperature overnight. Ethyl ether (100 ml) was added to extract product. Organic phase was combined and dried over MgSO$_4$. 14.32 g product as white solid (100% yield) was obtained by removing the solvent. NMR (400 MHz, CDCl$_3$) δ3.52 (s, 3H), 3.35 (s, 3H), 2.61 (s, 3H).

Method 42

2,6-Dichloro-N-(5-methoxy-1H-pyrazol-3-yl)pyrimidin-4-amine

To a solution of 2,4,6-trichloro-pyrimidine (1.7 g) in absolute ethanol (100 mL) was added DIEPA (4.1 mL) and 5-methoxy-1H-pyrazol-3-amine hydrogen chloride salt (1.46 g). The resulting solution was stirred at room temperature for over night. The solvent was evaporated under reduced pressure. The crude compound was purified by Gilson (10-60% MeCN/H$_2$O, 15 minutes) to give the titled compound as solid (1.23 g). $^1$H NMR δ 12.19 (s, 1H) 10.68 (s, 1H) 6.76 (s, 1H) 5.40 (s, 1H) 3.82 (s, 3H); m/z 260.

Method 43

2,5,6-Trichloro-N-(5-methoxy-1H-pyrazol-3-yl)pyrimidin-4-amine

To a solution of 2,4,5,6-tetrachloro-pyrimidine (2.18 g) in absolute ethanol (100 mL) was added DIEPA (4.4 mL) and 5-methoxy-1H-pyrazol-3-amine hydrogen chloride salt (1.50 g). The resulting solution was stirred at room temperature for over night. The solvent was evaporated under reduced pressure. The crude compound was purified by Gilson (10-60% MeCN/H$_2$O, 15 minutes) to give the titled compound as solid (0.76 g). m/z 294.

Method 44

2-Chloro-5-fluoro-N-(5-methyl-1H-pyrazol-3-yl)-6-morpholin-4-ylpyrimidin-4-amine To a solution of 2,4,6-trichloro-5-fluoropyrimidine (4.03 g) in absolute ethanol (100 mL) was added DIEPA (5.3 mL) and 5-methyl-1H-pyrazol-3-amine (2.03 g). The resulting solution was stirred at room temperature for 6 hours. The precipitation was filtered and washed with cold ethanol. The compound was dried by vacuum oven give 2,6-dichloro-5-fluoro-N-(5-methyl-1H-pyrazol-3-yl)pyrimidin-4-amine as solid (3.7 g). m/z 262. A mixture of morpholine (0.181 mL), 2,6-dichloro-5-fluoro-N-(5-methyl-1H-pyrazol-3-yl)pyrimidin-4-amine (500 mg) and DIPEA (0.505 ml) in absolute ethanol (10.0 ml) was heated at 80° C. for 5 hours. The solvent was removed under reduced pressure and the residue was purified by Gilson (10-50% MeCN/H$_2$O, 15 minutes) to give the titled compound as solid (236 mg). $^1$H NMR δ 12.05 (bs, 1H) 9.57 (s, 1H) 6.21 (s, 1H) 3.67 (t, 4H) 3.57 (t, 4H) 2.22 (s, 3H); m/z 313.

Method 45

N-(5-Methoxy-1H-pyrazol-3-yl)-2-(methylsulfonyl)-6-(trifluoromethyl)pyrimidin-4-amine To a solution of 4-chloro-2-(methylthio)-6-(trifluoromethyl)pyrimidine (2.29 g) in absolute ethanol (50 mL) was added DIEPA (4.4 mL) and 5-methoxy-1H-pyrazol-3-amine hydrogen chloride salt (1.46 g). The resulting solution was heated at 90° C. for over night. The solvent was evaporated under reduced pressure. The crude compound was purified by Gilson (10-60% MeCN/H$_2$O, 15 minutes) to give N-(3-methoxy-1H-pyrazol-5-yl)-2-(methylthio)-6-(trifluoromethyl) pyrimidin-4-amine as solid (0.64 g). m/z 306. N-(3-methoxy-1H-pyrazol-5-yl)-2-(methylthio)-6-(trifluoromethyl) pyrimidin-4-amine (240 mg) was dissolved in methylene chloride (5 mL), MCPBA (529 mg) was added. The resulting solution was stirred at room temperature for 0.5 hours and separate between methylene chloride and saturated sodium carbonate water solution. The organic layer was dried and solvent was removed under reduced pressure and low temperature. The crude product (270 mg) was carried on to do next step without further purification. m/z 338.

Method 46

2-Chloro-5-fluoro-N-(5-methoxy-1H-pyrazol-3-yl)-6-morpholin-4-ylpyrimidin-4-amine To a solution of 2,4,6-trichloro-5-fluoropyrimidine (2.01 g) in absolute ethanol (50 mL) was added DIEPA (4.4 mL) and 5-methoxy-1H-pyrazol-3-amine (2.24 g). The resulting solution was stirred at room temperature for over night. The solvent was removed by reduced pressure and the residue was purified by Gilson (10-50% MeCN/H$_2$O, 15 minutes) to give the titled compound 2,6-dichloro-5-fluoro-N-(5-methoxy-1H-pyrazol-3-yl)pyrimidin-4-amine as solid (0.776 g). m/z 278. A mixture of morpholine (0.256 mL), 2,6-dichloro-5- fluoro-N-(5-methoxy-1H-pyrazol-3-yl)pyrimidin-4-amine (776 mg) and DIPEA (0.742 ml) in n-butanol (14.0 ml) was heated at 90° C. for 5 hours. The solvent was removed under reduced pressure and the residue was purified by Gilson (10-50% MeCN/H$_2$O, 15 minutes) to give the titled compound as solid (310 mg). $^1$H NMR 9.80 (s, 1H) 5.66 (s, 1H) 3.77 (s, 3H) 3.64-3.71 (m, 4H) 3.53-3.64 (m, 4H); m/z 329.

Method 47

N-{2,5-Dichloro-6-[(5-methyl-1H-pyrazol-3-yl)amino]pyrimidin-4-yl}-N-methylmethanesulfonamide Following a procedure similar to that of Method 32, the title compound was prepared from N-(2,5,6-trichloro-pyrimidin-4-yl)-N-methylmethanesulfonamide (Method 48). MS: 351 (M+1).

Method 48

N-(2,5,6-Trichloro-pyrimidin-4-yl)-N-methyl-methanesulfonamide

Following a procedure similar to that of Method 32, the title compound was prepared from N-methylmethanesulfonamide and 2,4,5,6-tetrachloropyrimidine. MS: 290 (M+1).

Method 49

N-{2,5-Dichloro-6-[(5-isopropoxy-1H-pyrazol-3-yl)amino]pyrimidin-4-yl}-N,N',N'-trimethylsulfamide Following a procedure similar to that of Method 29, the title compound was prepared from N,N,N'-trimethyl-N'-(2,5,6-trichloropyrimidin-4-yl)sulfamide (Method 26). MS: 424 (M+1).

Method 50

5-Fluoropyrimidine-2-carbaldehyde

To a solution of 5-fluoropyrimidine-2-carbonitrile (Method 6, 1.0 g, 8.1 mmol) in anhydrous THF at −78° C. was added a solution of DIBAL-H (8.1 mL) over a period of 20 minutes. The resulting mixture was stirred at this temperature for 2 hours whereupon MeOH was added. The solution was allowed to warm to room temperature whereupon a solution of conc. HCl was added. The resulting mixture was stirred for 2 hours at ambient temperature and the aqueous layer was washed with EtOAc (3×). The combined organic extracts were washed with brine and dried (MgSO$_4$). Evaporation of the solvent afforded the titled compound (780 mg, 76%). MS: [M+H]$^+$ 127.

Method 51

N-[(5-Fluoropyrimidin-2-yl)methylene]-2-(R)-methylpropane-2-sulfinamide

To a solution of 5-fluoropyrimidine-2-carbaldehyde (Method 50, 1.55 g, 12.3 mmol) in anhydrous DCM at room temperature were added 2-(R)-methylpropane-2-sulfinamide (1.79 g, 14.7 mmol) and anhydrous copper(II) sulphate (1.96 g, 12.28 mmol). The resulting mixture was stirred at this temperature for 24 hours, the solid was filtered under vacuum, washed with DCM (3×) and evaporation of the solvents afforded a yellow oil. The resulted residue was purified by column chromatography (Hex-EtOAc=3:1) to give the title compound (1.94 g, 69%). 1H NMR (300 MHz, DMSO-D6) ppm 9.13 (s, 2H) 8.47 (s, 1H) 0.99 (s, 9H). MS:[M+H]$^+$ 232. The procedure described in Method 51 may be used to obtain N-[(5-fluoropyrimidin-2-yl)methylene]-2-(S)-methylpropane-2-sulfinamide by replacing 2-(R)-methylpropane-2-sulfinamide with 2-(S)-methylpropane-2-sulfinamide as a starting material.

Method 52

N-[(1S)-1-(5-Fluoropyrimidin-2-yl)ethyl]-(2R)-methylpropane-2-sulfinamide

To a solution of N-[(5-fluoropyrimidin-2-yl)methylene]-2-(R)-methylpropane-2-sulfinamide (Method 51, 1.94 g, 8.5 mmol) in anhydrous THF at −20° C. was added slowly a solution of MeMgBr (9.3 mL g, 9.3 mmol). The resulting mixture was stirred at this temperature for 3 hours whereupon it partitioned between H$_2$O and EtOAc. The aqueous layer was extracted with EtOAc (3×) washed with brine, dried (MgSO$_4$). Evaporation of the solvents under reduced pressure under vacuum afforded yellow oil. The resulted residue was purified by column chromatography (100% EtOAc) to give the title compound (660 mg, 50%). $^1$H NMR (300 MHz, DMSO-D6) ppm 8.89 (s, 2H) 5.53 (d, 1H) 4.43-4.65 (m, 1H) 1.46 (d, 3H) 1.11 (s, 9H). MS:[M+H]$^+$246

The procedure described in Method 52 may be used to obtain N-[(1S)-1-(5-fluoropyrimidin-2-yl)ethyl]-(2S)-methylpropane-2-sulfinamide by replacing N-[(5-fluoropyrimidin-2-yl)methylene]-2-(R)-methylpropane-2-sulfinamide with N-[(5-fluoropyrimidin-2-yl)methylene]-2-(S)-methylpropane-2-sulfinamide as a starting material.

Method 53

(S)-1-(5-Fluoropyrimidin-2-yl)ethanamine hydrochloride

To a solution of N-[(1S)-1-(5-fluoropyrimidin-2-yl)ethyl]-(2R)-methylpropane-2-sulfinamide (Method 52, 655 mg, 2.67 mmol) in dry dioxane (20 ml) was added HCl (3.4 ml, 13.3 mmol) in dioxane. The reaction was stirred at room temperature for 3 hours. The solvent was removed to give the title compound as white solid (quantitative). MS: Calcd.: 141. Found: [M+H]$^+$142.

(S)-1-(5-Fluoropyrimidin-2-yl)ethanamine hydrochloride may also obtained using the process described in Method 53 by replacing N-[(1S)-1-(5-fluoropyrimidin-2-yl)ethyl]-(2R-methylpropane-2-sulfinamide with N-[(1S)-1-(5-fluoropyrimidin-2-yl)ethyl]-(2S)-methylpropane-2-sulfinamide as a starting material.

Utility

The compounds of the present invention have utility for the treatment of cancer by inhibiting the tyrosine kinases, particularly the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumours of the central and peripheral nervous system, and other tumour types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8; 21), autocrine or paracrine signalling leading to elevated serum levels of NGF, BDNF, neurotrophins or tumours with constitutively active Trk associated with disease aggressiveness, tumour growth and proliferation or survival signalling.

Compounds of the present invention have been shown to inhibit tyrosine kinases, particularly the Trks and more particularly Trk A and B, as determined by the Trk A Assay described herein.

Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention.

Trk A Assay Format

Trk A kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number P04629) was expressed in SF9 cells and purified using standard nickel column chromatography. After incubation of the kinase with a biotinylated substrate and adenosine triphosphate (ATP) for 20 minutes at room temperature, the kinase reaction was stopped by the addition of 30 mM ethylenediaminetetraacetic acid (EDTA). The reaction was performed in 384 well microtitre plates and the reaction products were detected with the addition of strepavidin coated Donor Beads and phosphotyrosine-specific antibodies coated Acceptor Beads using the EnVision Multilabel Plate Reader after an overnight incubation at room temperature.

| | |
|---|---|
| Peptide substrate | PolyEY-biotin (PGT-bio.) |
| ATP Km | 70 µM |
| Assay conditions | 0.838 ng/ml Trk A, 9 mM HEPES, 45 µg/ml BSA, 10 mM MnCl₂, 5 nM PGT-bio, 0.01% Triton ® X-100, 70 µM ATP |
| Incubation | 20 minutes, room temperature |
| Termination/Detection conditions | 6.3 mM HEPES, 30 mM EDTA, 525 µg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nM Emission = 570 nM Excitation Time = 180 ms Total Measurement Time = 550 ms |

Although the pharmacological properties of the compounds of the formula (I) vary with structural change, in general activity possessed by compounds of the formula (I) may be demonstrated at $IC_{50}$ concentrations (concentrations to achieve 50% inhibition) or doses in the range of (0.01 µM to 10 µM).

When tested in the above in-vitro assay the Trk inhibitory activity of the following example was measured at the following $IC_{50}$s.

| Ex | $IC_{50}$ (µM) |
|---|---|
| 1 | 0.033 |

The compounds of the present invention have utility for the treatment of myeloproliferative disorders, myelodysplastic syndrome and cancer by inhibiting the tyrosine kinases, particularly the JAK family and more particularly JAK2. Methods of treatment target tyrosine kinase activity, particularly the JAK family activity and more particularly JAK2 activity, which is involved in a variety of myeloproliferative disorders, myelodysplastic syndrome and cancer related processes. Thus, inhibitors of tyrosine kinase, particularly the JAK family and more particularly JAK2, are expected to be active against myeloproliferative disorders such as chronic myeloid leukemia, polycythemia vera, essential thrombocythemia, myeloid metaplasia with myelofibrosis, idiopathic myelofibrosis, chronic myelomonocytic leukemia and hypereosinophilic syndrome, myelodysplastic syndromes and neoplastic disease such as carcinoma of the breast, ovary, lung, colon, prostate or other tissues, as well as leukemias, myelomas and lymphomas, tumours of the central and peripheral nervous system, and other tumour types such as melanoma, fibrosarcoma and osteosarcoma. Tyrosine kinase inhibitors, particularly the JAK family inhibitors and more particularly JAK2 inhibitors are also expected to be useful for the treatment other proliferative diseases including but not limited to autoimmune, inflammatory, neurological, and cardiovascular diseases.

The compounds of the present invention have been shown to inhibit tyrosine kinases, particularly the JAK family and more particularly JAK2, as determined by the JAK2 Assay described herein.

The compounds provided by this invention should also be useful as standards and reagents in determining the ability of a potential pharmaceutical to inhibit tyrosine kinases, particularly the JAK family and more particularly JAK2. These would be provided in commercial kits comprising a compound of this invention.

JAK2 Assay

JAK2 kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure JAK2 kinase activity, commercially available purified enzyme, C-terminal His6-tagged, recombinant, human JAK2, amino acids 808-end, (Genbank Accession number NM 004972) expressed by baculovirus in Sf21 cells from Upstate Biotechnology #14-640 was used. After incubation of the kinase with a biotinylated substrate and adenosine triphosphate (ATP) for 60 minutes at room temperature, the kinase reaction was stopped by the addition of 30 mM ethylenediaminetetraacetic acid (EDTA). The reaction was performed in 384 well microtitre plates and the reaction products were detected with the addition of streptavidin coated Donor Beads and phosphotyrosine-specific antibodies coated Acceptor Beads using the EnVision Multilabel Plate Reader after an overnight incubation at room temperature.

| | |
|---|---|
| Peptide substrate | TYK2 (Tyr 1054/1055 biotinylated peptide) Cell Signalling Technology #2200B. 402uM stock. |
| ATP Km | 30 μM |
| Assay conditions | 150 pM JAK2 enzyme, 30uM ATP, 80 nM Tyk2, 10 mM MgCl$_2$, 50 mM Hepes buffer pH 7.5, 1 mM DTT, 0.025% DTT. |
| Incubation | 60 minutes, room temperature |
| Termination/Detection conditions | 6.3 mM HEPES, 30 mM EDTA, 525 μg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nM Emission = 570 nM Excitation Time = 180 ms Total Measurement Time = 550 ms |

When tested in the above in-vitro assay the JAK inhibitory activity of the following example was measured at the following IC$_{50}$.

| Ex | IC$_{50}$ (nM) |
|---|---|
| 7 | 3.9 |

The invention claimed is:

1. 5-Chloro-N$^2$-[(1S)-1-(5-fluoropyrimidin-2-yl)ethyl]-N$^4$-(5-methyl-1H-pyrazol-3-yl)pyrimidine-2,4-diamine or a pharmaceutically acceptable salt thereof.

2. 5-Chloro-N$^2$-[(1S)-1-(5-fluoropyrimidin-2-yl)ethyl]-N$^4$-(5-methyl-1H-pyrazol-3-yl)pyrimidine-2,4-diamine.

3. A pharmaceutically acceptable salt of 5-Chloro-N$^2$-[(1S)-1-(5-fluoropyrimidin-2-yl)ethyl]-N$^4$-(5-methyl-1H-pyrazol-3-yl)pyrimidine-2,4-diamine.

4. A pharmaceutical composition comprising 5-Chloro-N$^2$-[(1S)-1-(5-fluoropyrimidin-2-yl)ethyl]-N$^4$-(5-methyl-1H-pyrazol-3-yl)pyrimidine-2,4-diamine or a pharmaceutically acceptable salt thereof of claim 1 and at least one pharmaceutically acceptable carrier, diluent, or excipient.

5. A pharmaceutical composition comprising 5-Chloro-N$^2$-[(1S)-1-(5-fluoropyrimidin-2-yl)ethyl]-N$^4$-(5-methyl-1H-pyrazol-3-yl)pyrimidine-2,4-diamine of claim 2 and at least one pharmaceutically acceptable carrier, diluent, or excipient.

6. A pharmaceutical composition comprising a pharmaceutically acceptable salt of 5-Chloro-N$^2$-[(1S)-1-(5-fluoropyrimidin-2-yl)ethyl]-N$^4$-(5-methyl-1H-pyrazol-3-yl)pyrimidine-2,4-diamine of claim 3 and at least one pharmaceutically acceptable carrier, diluent, or excipient.

* * * * *